United States Patent [19]

Khambay et al.

[11] Patent Number: 5,962,002

[45] Date of Patent: Oct. 5, 1999

[54] PESTICIDAL COMPOUNDS

[75] Inventors: Bhupinder Pall Singh Khambay, Southall; Duncan Batty, Kempston; Stuart Cameron, Luton; David Gordon Beddie, Milton Keynes, all of United Kingdom

[73] Assignee: BTG International Limited, London, United Kingdom

[21] Appl. No.: 08/891,096

[22] Filed: Jul. 10, 1997

Related U.S. Application Data

[63] Continuation of application No. PCT/GB96/00042, Jan. 10, 1996

[60] Provisional application No. 60/001,100, Jul. 13, 1995, provisional application No. 60/001,099, Jul. 13, 1995, and provisional application No. 60/001,102, Jul. 13, 1995.

[30] Foreign Application Priority Data

| Jan. 10, 1995 | [GB] | United Kingdom | ................. 9500389 |
|---|---|---|---|
| Jan. 10, 1995 | [GB] | United Kingdom | ................. 9500390 |
| Jan. 10, 1995 | [GB] | United Kingdom | ................. 9500392 |
| Jan. 10, 1995 | [GB] | United Kingdom | ................. 9500394 |
| Jul. 4, 1995 | [GB] | United Kingdom | ................. 9513573 |
| Jul. 4, 1995 | [GB] | United Kingdom | ................. 9513584 |
| Jul. 4, 1995 | [GB] | United Kingdom | ................. 9513594 |
| Jul. 4, 1995 | [GB] | United Kingdom | ................. 9513595 |
| Nov. 13, 1995 | [GB] | United Kingdom | ................. 9523165 |

[51] Int. Cl.$^6$ .......................... A01N 25/06; A01N 57/20; C07F 9/50; C07C 34/17

[52] U.S. Cl. ................. 424/405; 514/75; 568/15; 568/735; 568/736; 568/737

[58] Field of Search .................... 568/735, 736, 568/737, 15; 424/405

[56] References Cited

U.S. PATENT DOCUMENTS 4,110,473  8/1978  Fugitt et al. ......................... 424/331

FOREIGN PATENT DOCUMENTS

WO 95/32176  11/1995  WIPO.

OTHER PUBLICATIONS

L.F. Fieser et al, "Naphtoquinone antimalarials II. Correlation of structure and activity against P. lophurae in ducks", Nov. 2, 1948, pp. 3156–3165.

"Janssen Chimica", 1986, Janssen Pharmaceutica, p. 162, No. 15.926.18 and p. 1034, No. 14.000.32 and 14.002.34.

*Primary Examiner*—Johann Richter
*Assistant Examiner*—Dominic Keating
*Attorney, Agent, or Firm*—Nixon & Vanderhye

[57] ABSTRACT

This invention relates to 1,1,1,4-substituted naphthaline compounds, compositions, processes for their preparation and processes for their use as pesticides, especially insecticides, acaricides and fungicides.

41 Claims, No Drawings

PESTICIDAL COMPOUNDS

This application is a continuation of PCT/GB96/00042, filed Jan. 10, 1996, now pending, which claims the benefit of U.S. Provisional Application Nos. 60/001,100, 60/001,099 and 60/001,102, all filed Jul. 13, 1995.

The present invention relates to novel 1,2,3,4-substituted naphthalene compounds having utility as pesticides, particularly as insecticides, acaricides and fungicides; to methods for preparation of these compounds; to compositions containing them and to use of the compounds and compositions for the control of pests.

U.S. Pat. No. 2,572,946 discloses a composition for the control of mites and aphids in which the active ingredient is a compound of the general formula (P1)

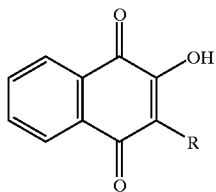

(P1)

where R is a radical, containing from 6 to 15 carbon atoms, selected from alkyl, cyclohexyl and cyclohexylalkyl groups; n-alkyl, iso-alkyl, alkylcycloalkyl and aralkyl groups are exemplified but no specific miticidal or aphicidal data being given for them.

DE 2641343 A1 generically discloses compounds of the general formula (P2)

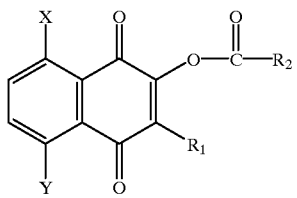

(P2)

in which $R_1$ is a straight, branched or cyclic $C_{8-14}$ alkyl group, $R_2$ is a straight or branched $C_{1-17}$ alkyl, $C_{2-17}$ alkenyl, $C_{3-6}$ cycloalkyl, $C_{1-4}$ alkoxy, $-CH_2OCH_3$, $-CH_2OCH_2CH_3$ or $-CH=CH-COOH$ group, and X and Y represent a hydrogen, fluorine, chlorine or bromine atom or a methyl or methoxy group. These compounds are said to exhibit acaricidal and aphicidal activity but only compounds where $R_1$ is a linear $C_8$ or $C_{11-14}$ alkyl group are shown to have such activity.

U.S. Pat. No. 4,110,473 concerns a method for protecting plants from mites (acarids) which comprises treating the plant with a compound of the general formula (P3)

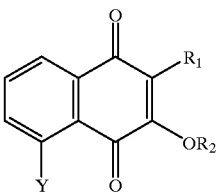

(P3)

where Y is hydrogen, fluorine, chlorine or bromine; $R_1$ is branched, cyclic or straight chain $C_{8-14}$ alkyl; $R_2$ is branched or straight chain $C_{1-12}$ saturated alkyl or $C_{3-12}$ unsaturated alkyl optionally substituted by one or two chlorine, bromine, methoxy or ethoxy substituents, or $C_{3-6}$ cycloalkyl.

DE 3801743 A1 generically discloses compounds of the general formula (P4)

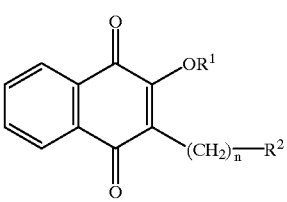

(P4)

in which n is 0 to 12, $R^1$ represents hydrogen or an optionally substituted alkyl, aralkyl, alkylcarbonyl, (hetero)arylcarbonyl, alkoxycarbonyl, alkylsulphonyl or arylsulphonyl group, and $R^2$ represents a haloalkyl, optionally substituted (hetero)aryl or substituted cycloalkyl group. These compounds are said to exhibit acaricidal and fungicidal activity.

Ten compounds of formula (P4) are specifically disclosed in which n is 0, $R^1$ is a hydrogen atom and $R^2$ is a 4-(t-butyl)cyclohexyl, 4-(trimethylsilyl)cyclohexyl, 4-(cyclohexyl)-cyclohexyl, 2-trifluoromethylcyclohexyl or 3,5-di(trifluoromethyl)-cyclohexyl group or n is 0, $R^1$ is an ethanoyl group and $R^2$ is a 4-(t-butyl)cyclohexyl, 4-(cyclohexyl)cyclohexyl, 2- or 3-trifluoromethylcyclohexyl or 3,5-di(trifluoromethyl)-cyclohexyl group. Of these, acaricidal activity is demonstrated for two compounds of formula (P4) in which n is 0, $R^1$ is a hydrogen atom and $R^2$ is a 4-(t-butyl)cyclohexyl or 4-(trimethylsilyl)-cyclohexyl group.

EP 0077550 discloses compounds of general formula (P5)

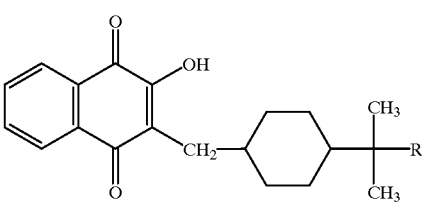

(P5)

in which R is an alkyl group of from 1 to 10 carbon atoms and describes their use in veterinary formulations, particularly for prophylaxis against protozoan infection.

None of the published prior art relates to insecticidal or acaricidal naphthoquinone compounds wherein a quaternary carbon atom is linked either directly to the naphthoquinone ring or linked to it through an n- or iso-alkyl group.

Copending international application No. PCT/GB95/00953 relates to naturally occurring compounds of the general formula (P6)

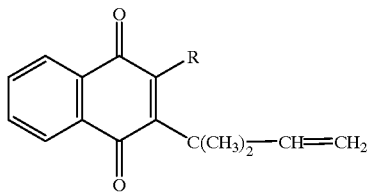

(P6)

in which R represents a hydrogen atom or a hydroxyl or an ethanoyloxy group, and to their use as pesticides, especially fungicides, insecticides and/or acaricides. These compounds were previously disclosed as plant metabolites by Chamy et al., (1993) *Bol. Soc. Chil. Quim.* 38 187–190.

Fieser et al. J.A.C.S. Vol. 70, No. 6 (1948) disclose the preparation of 2-alkyl-3-hydroxynaphthalene-1,4-diones where the alkyl groups include quaternary carbons but ascribe no pesticidal activity to these with respect to fungi, insects or acarids. This document is concerned with anti-protozoan activity and the quaternary compounds are among the least active disclosed.

Santisopasri et al. Biosci. Biotech. Biochem. 59(10) 1999–2000 (1995) and Annual Meeting of the Pesticide Science Society of Japan, Tokyo, March 1993, p55, describe a naturally occurring anti-fungal napthhalene-1,4-dione where the alkyl group comprises a 2,6-dimethyl-2,6-octadienoxy 2,2-dimethylpropyl group and the corresponding 2,2-dimethyl 3-hydroxypropyl group metabolite.

The present inventors have now developed synthetic naphthoquinones and related compounds having advantageous pesticidal properties as compared to those already known in the art, particularly as applied to the treatment of specific pests of fungal, insect and/or acarid nature. Preferred synthetic compounds of the invention have excellent pesticidal activity against, inter alia, whitefly and/or mites and/or aphids and/or fungi; most preferred compounds showing useful activity against at least two, and preferably all, of these. Many of the compounds of the present invention also exhibit anti-feedant activity against at least some insects or acarids.

According to a first aspect of the present invention there is provided a compound of general formula (I)

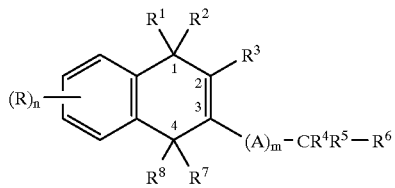

(I)

or a salt thereof, in which
n represents an integer from 0 to 4; m represents an integer 0 or 1;
each R independently represents a halogen atom or a nitro, cyano, hydroxyl, alkyl, alkenyl, haloalkyl, haloalkenyl, alkoxy, haloalkoxy, haloalkenoxy, amino, alkylamino, dialkylarnino, alkoxycarbonyl, carboxyl, alkanoyl, alkylthio, alkylsulphinyl, alkylsulphonyl, carbarnoyl, alkylarnido, cycloalkyl, aryl or aralkyl group; characterised in that $R^1$ and $R^2$ each independently represent an optionally substituted alkoxy group or together represent a group =O, =S or =N—$OR^9$, where $R^9$ represents a hydrogen atom or an optionally substituted alkyl group;
$R^3$ represents a hydroxyl group, or a group —OL where L is a leaving group, or a group which in vivo is transformed into a group —$OL^1$ where $L^1$ is a leaving group; $R^6$ represents an optionally substituted alkyl, alkenyl, alkynyl, cycloalkyl, cycloalkenyl, aryl, alkoxy, alkenyloxy, alkynyloxy, cycloalkyloxy, cycloalkenyloxy or aryloxy group;
$R^7$ and $R^8$ independently represent an optionally substituted alkoxy group or together represent a group =O, =S or =N—$OR^9$, where $R^9$ is as previously defined; and
wherein R4 and $R^5$ each independently represent a halogen atom or an optionally substituted alkyl or alkenyl group, or together with the interjacent carbon atom represent an optionally substituted cycloalkyl or cycloalkenyl ring; and A represents a straight or branched chain alkyl or alkenyl group, which may be optionally susbtituted, preferably with halogen, an acyclic carbon chain of which links the 3 position of the naphthalene ring shown and the moiety —$CR^4R^5R^6$; with the provisos that when $R^1$ with $R^2$, and $R^7$ with $R^8$, are groups =O, n=0, (i) when $R^4$ and $R^5$ are methyl m is 0 and $R^6$ is ethenyl, then $R^3$ is not hydroxyl or ethanoyloxy, (ii) when $R^4$ and $R^5$ are methyl, m is 0 or m is 1 when A is —$CH_2$— or —$(CH_2)_2$— and $R^3$ is hydroxyl then $R^6$ is not methyl, (iii) when $R^4$ and $R^5$ are methyl, m is 1 where A is —$(CH_2)_2$— and $R^3$is hydroxyl then $R^6$ is not chloro (iv) when $R^4$ and $R^5$ together with the interjacent carbon atom form a cyclohexyl ring, m is 1 when A is —$CH_2$— and $R^3$ is hydroxyl $R^6$ is not methyl and (v) when $R^4$ and $R^5$ are methyl, m is 1 A is —$CH_2$—and $R^3$ is hydroxyl $R^6$ is not hydroxytmethyl or the 2,6-dimethyl-2, 6-octadienoate ester thereof.

When the compounds of formula I contain a group defined as an alkyl, alkenyl or alkynyl substituent otherwise undefined, this may be linear or branched and may contain up to 12, preferably up to 6 and especially up to 4, carbon atoms. A cycloalkyl or cycloalkenyl group may contain from 3 to 10, but most preferably contains 5 to 8 carbon atoms. An aryl group may be any aromatic hydrocarbon group, especially a phenyl or naphthyl group. An aralkyl group may be any alkyl group as defined above which is substituted by an aryl group as defined above, especially a benzyl group optionally substituted with an alkyl group.

When any of the foregoing substituents are designated as being optionally substituted, the substituent groups which are optionally present may be any one or more of those customarily employed in the development of pesticidal compounds and/or the modification of such compounds to influence their activity, persistence, penetration or other property. Specific examples of such substituents include, for example, halogen atoms, nitro, cyano, hydroxyl, alkyl, alkenyl, haloalkyl, haloalkenyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, phenyl and benzyl groups. Typically, 0–3 substituents may be present. When any of the foregoing substituents represents or contains an alkyl substituent, this may be linear or branched and may contain up to 12, preferably up to 6, and most preferably up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, alkenyl, haloalkyl, haloalkenyl, alkoxy or haloalkoxy groups. Preferably, the aryl moiety is a phenyl moiety and the cycloalkyl moiety contains from 3 to 8, preferably 4 to 7, carbon atoms.

It is preferred that R, if present, represents a halogen atom or a nitro, cyano, hydroxyl, $C_{1-4}$ alkyl, $C_{1-4}$ haloalkyl, $C_{2-4}$ alkenyl, $C_{2-4}$ haloalkenyl, $C_{1-4}$ alkoxy, $C_{1-4}$ haloalkoxy, $C_{1-4}$ alkylamino, di—$C_{1-4}$ alkylamino, $C_{14}$ alkoxycarbonyl, $C_{1-4}$ alkylthio, $C_{1-4}$ alkylsulphinyl or $C_{1-4}$ alkylsulphonyl group.

More preferably, R, if present, represents a halogen atom or a $C_{1-4}$ alkyl, $C_{1-4}$ haloalkyl, $C_{2-4}$ alkenyl, $C_{2-4}$ haloalkenyl, $C_{1-4}$ alkoxy or $C_{1-4}$ haloalkoxy group.

Preferably, n is 0, 1 or 2 and it is especially preferred that n is 0.

It is also preferred that $R^1$ and $R^2$ each independently represent a $C_{1-4}$ alkoxy, especially a methoxy, group or together represent a group =O or =N—$OR^9$, where $R^9$ represents a hydrogen atom or a $C_{1-4}$ alkyl, especially a methyl, group. It is especially preferred that $R^1$ and $R^2$ are both methoxy or together represent a group =O.

When $R^3$ is a group —OL where L is a leaving group, or a group which in vivo is transformed into a group —$OL^1$, the leaving group may be any group customarily employed as a leaving group. It is preferred that the leaving group is such that the $pK_a$ value of the acid LOH in water is from 1 to 7, more preferably from 1 to 6 and especially from 1 to 5.

When $R^3$ represents a group which in vivo is transformed into a group —$OL^1$ where $L^1$ is a leaving group, it is preferred that the transformation is carried out in a plant to be protected or a pest to be combated, preferably by action of enzymes within the plant or pest. For instance, if $R^3$ represents a β-acid group, such as —O—$CH_2CH_2CO$—OH where —$CH_2CH_2CO$—OH is not a leaving group, it may be subjected to enzymatic oxidation in vivo to form a group —O—CO—$CH_2$—CO—OH, eg. by a β-oxidase, where —CO—$CH_2$—CO—OH is a leaving group.

Preferably, $R^3$ represents a group —$OR^{10}$ where $R^{10}$ represents a hydrogen atom, an optionally substituted alkyl, alkenyl, aryl or aralkyl group, or a group —CO—$R^{11}$, —CO—O—$R^{11}$, —$SOR^{11}$, —$SO_2$—$R^{11}$, —P(X)($OR^{12}$)($OR^{13}$), —P(X)($R^{12}$)($OR^{13}$), —P($OR^{12}$)($OR^{13}$) or —P($R^{12}$)($OR^{13}$) where $R^{11}$ represents a hydrogen atom, an optionally substituted alkyl, alkenyl, aryl or aralkyl group or a group —$NR^{12}R^{13}$; $R^{12}$ and $R^{13}$ independently representing a hydrogen atom or an optionally substituted alkyl group and X represents an oxygen or sulphur atom. Where $R^{10}$ or $R^{11}$ represents an optionally substituted aryl or aralkyl group, it is preferred that the aryl group is a phenyl group and that the optional substituents are selected from halogen atoms, nitro and $C_{1-4}$ alkyl groups. Substitution at the 4-position of the phenyl ring is particularly preferred. For the purposes of $R^3$, the term optionally substituted includes, eg. substitution with silicon containing groups, eg. trialkylsilyl groups such as trimethylsilyl, as a substituent on $R^{10}$, $R^{11}$ or $R^{12}$.

Preferably $R^3$ represents a hydroxyl group or a group —O—CO—$R^{11}$, —O—CO—$OR^{11}$ where $R^{11}$ represents a hydrogen atom or a $C_{1-12}$ alkyl, $C_{1-12}$ haloalkyl, $C_{1-12}$ hydroxyalkyl, $C_{1-12}$ carboxyalkyl, phenyl or benzyl group.

It is particularly preferred that $R^3$ represents a group —OH or —O—CO—$R^{11}$, where $R^{11}$ represents a hydrogen atom or a $C_{1-6}$ alkyl, $C_{1-6}$ haloalkyl, phenyl or benzyl group. Most preferred for $R^{11}$ is a methyl, ethyl, propyl or butyl group.

Preferably $R^6$ represents a $C_{1-16}$ alkyl, $C_{2-16}$ alkenyl, $C_{1-16}$ haloalkyl, $C_{2-16}$ haloalkenyl, $C_{1-16}$ alkanoylalkyl, $C_{1-16}$ alkoxyalkyl, $C_{1-6}$ alkoxy, $C_{1-16}$ haloalkoxy or $C_{1-16}$ alkoxyalkoxy group. More preferably these groups are of $C_{1-6}$ in length, or $C_{2-6}$ in length in the case of alkenyls.

Still more preferably, $R^6$ represents a $C_{1-6}$ alkyl, especially methyl or ethyl, $C_{1-6}$ haloalkyl, eg. trifluoromethyl, difluoromethyl or monofluoromethyl group, or $C_{2-6}$ alkenyl or $C_{2-6}$ haloalkenyl.

Preferably, $R^7$ and $R^8$ independently represent a $C_{1-4}$ alkoxy group or together represent a group =O or =N—$OR^9$, where $R^9$ represents a hydrogen atom or a $C_{1-4}$ alkyl group, but it is especially preferred that $R^7$ and $R^8$ are both methoxy or together represent a group =O.

It will be realised by those skilled in the art that compounds wherein $R^1$ and $R^2$, and $R^7$ and $R^8$ are each alkoxy, or together are =S or a group $NOR^9$ will be potential biological precursors for the corresponding naphthoquinones, the naphthoquinones being the preferred compounds of the invention.

Preferably, $R^4$ and $R^5$ each independently represent a $C_{1-4}$ alkyl, $C_{1-4}$ haloalkyl, $C_{2-4}$ alkenyl or $C_{2-4}$ haloalkenyl group or, together with the interjacent carbon atom, represent an optionally substituted cycloalkyl or cycloalkenyl ring, this ring preferably being optionally substituted with halogen, alkyl, haloalkyl, alkenyl or haloalkenyl.

The compounds of formula I may form salts, e.g. when $R^3$ represents a hydroxyl group. Suitable bases for forming such salts include inorganic bases, such as sodium hydroxide, potassium hydroxide or sodium carbonate, and organic bases, for example tertiary amines such as triethylamine and cyclic amines such as pyrrolidine.

It will be appreciated by those skilled in the art that many of the compounds of the present invention will exist as different geometric isomers and diastereomers. The scope of the present invention includes both the individual isomers and mixtures of these.

The present inventors have determined that the compounds of the present invention are of particular interest in so far as they show pesticidal activity against species and strains of pest that have developed resistance to currently commercial used pesticides. Thus the compounds of the present invention will have particular application against insect, acarid and fungal strains that are resistant to other commercially available pesticides. The present inventors have determined that the characteristic quaternary carbon atom which links groups $R^4$, $R^5$ and $R^6$ to either group A or the 3 position of the ring shown in formula I may be provided in at least three optional configurations in order to provide particular activity profiles suited to combating of particular groups of pests.

In a first preferred distinct group of compounds of the first aspect of the invention the quaternary carbon atom is provided immediately adjacent to the naphthalene ring in the form of a group —$CR^4R^5R^6$ wherein $R^4$ and $R^5$ independently represent a halogen or an optionally substituted alkyl or alkenyl group, excluding those compounds of copending PCT/GB95/00953 described previously and referred to in the proviso appended to the definitions of formula I.

In this first preferred distinct group compounds of general formula (II)

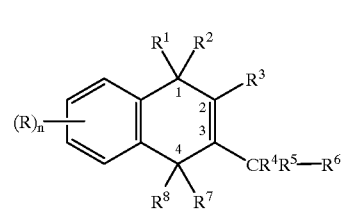

(II)

or a salt thereof are provided in which R, $R^1$, $R^2$, $R^3$, $R^6$, $R^7$ and $R^8$ and n are as defined for formula I and $R^4$ and $R^5$ represent a halogen or an optionally substituted alkyl or alkenyl group.

More preferred compounds of the general formula (II) are those where n is 0, $R^1$ with $R^2$, and $R^7$ with $R^8$ are both =O;

wherein $R^4$ and $R^5$ each independently represent a $C_{1-4}$ alkyl or $C_{1-4}$ haloalkyl group and $R^6$ represents a $C_{1-7}$ alkyl, $C_{1-7}$ haloalkyl, $C_{1-7}$ alkoxyalkyl, $C_{1-7}$ alkoxy, $C_{1-7}$ alkoxyalkoxy, $C_{2-7}$ alkenyl, $C_{2-7}$ haloalkenyl or $C_{2-7}$ alkoxyalkenyl group. $R^3$ is preferably OH, —O—CO—$R^{11}$ or —O—CO—O—$R^{11}$ wherein $R^{11}$ is $C_{1-3}$ alkyl, and most preferably —OH. Still more preferably $R^6$ represents a $C_{1-7}$ alkyl, $C_{2-7}$ alkenyl or $C_{1-7}$ haloalkyl or $C_{2-7}$ haloalkenyl group and most preferably $R^6$ represents a $C_{1-6}$ alkyl, $C_{1-6}$ haloalkyl, $C_2$ alkenyl or $C_2$ haloalkenyl group. Most preferably $R^4$ and $R^5$ are methyl.

It is found by the inventors that compounds of this first preferred group generally have effective pesticidal activity against insects, acarids and fuingi, and particularly against mites and whitefly. Particularly susceptible whitefly are Bemisia species.

In a second preferred distinct group of compounds of the first aspect of the invention the quaternary carbon atom is provided as part of a cycloalkyl or cycloalkenyl ring and thus this second group of preferred compounds of formula (1) are of preferred formula (III)

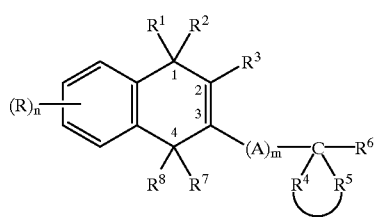

(III)

wherein
n, A, R, $R^1$, $R^2$, $R^3$, $R^6$, $R^7$ and $R^8$ are as defined for general formula (I);
m represents an integer 0 to 1;
and $R^4$ and $R^5$ together with the inteijacent carbon atom represent an optionally substituted cycloalkyl or cycloalkenyl group.

More preferably the compounds of this group are of formula (III) wherein $R^1$ with $R^2$, and $R^7$ with $R^8$ are both =O; n and m are 0; $R^4$ and $R^5$ together with the interacent carbon atom represent a fully saturated cycloalkyl ring which is optionally substituted; and $R^6$ represents a $C_{1-16}$ alkyl or $C_{2-16}$ alkenyl group optionally substituted by halogen. $R^3$ is preferably OH, —O—CO—$R^{11}$ or —O—CO—O—$R^{11}$ wherein $R^{11}$ is $C_{1-3}$ alkyl, and most preferably —OH Still more preferably $R^4$ and $R^5$ together with the inte jacent carbon atom represent a $C_{4-8}$ saturated cycloalkyl ring which is optionally substituted, most preferably with chlorine or fluorine; still more preferably being a $C_{5-8}$ cycloalkyl ring, and $R^6$ is a $C_{1-6}$ alkyl, $C_{2-6}$ alkenyl, $C_{1-6}$ haloalkyl group, $C_{2-6}$ haloalkenyl group or a halogen. Exceptionally active compounds of this group are those where $R^4$ and $R^5$ together with the interjacent carbon atom represent a cyclohexyl ring and $R^6$ is $C_{1-2}$ alkyl or $C_2$ alkenyl.

Preferred compounds of this second preferred group of the invention are particularly effective against mites and whitefly, as well as against certain fungi, with the most active compounds having exceptional activity against whitefly, particularly of Bemisia species while retaining activity against mites.

In a third distinct group of compounds of the first aspect of the invention the quaternary carbon atom is not in a cycloalkyl or cycloalkenyl group and is provided at between 2 and 16 carbon atoms length away from the naphthalene ring, more preferably between 2 and 10. Most preferably the quaternary carbon is between 4 and 8 carbon atoms length away from the naphthalene ring.

Thus in this distinct group preferred compounds of formula (I) are of preferred formula (IV)

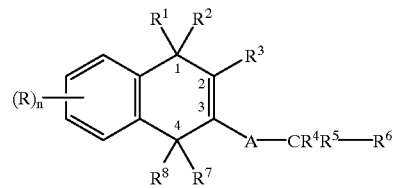

(IV)

wherein
n, A, R, $R^1$, $R^2$, $R^3$, $R^6$, $R^7$ and $R^8$ are as defined for general formula (I); and
$R^4$ and $R^5$ each independently represent a halogen or optionally substituted alkyl or alkenyl group.

For the purpose of combatting whitefly the group A preferably has a chain of between 3 and 7 carbon atoms between the naphthalene ring and the quaternary carbon atom, particularly when it is an unbranched alkylene chain.

For the purpose of providing high efficacy against aphids the group A preferably has a chain of between 4 and 8 carbon atoms between the naphthalene ring and the quaternary carbon atom, particularly when it is an unbranched alkylene chain.

For both these circumstances, the presence of one or more branch chains on the linking carbon chain of A will allow peak activity to be obtained using a shorter length chain between the naphthalene ring and quaternary carbon.

More preferred compounds of this group are of formula (IV) wherein $R^1$ with $R^2$, and $R^7$ with $R^8$ are both =O; m is 1, and A is a $C_{3-8}$ alkyl or alkenyl chain, which may be substituted by a halogen or a branch chain which may be halogenated Preferably $R^4$, $R^5$ and $R^6$ are $C_{1-6}$ alkyl or haloalkyl or $C_{2-6}$ alkenyl or haloalkenyl. $R^3$ is preferably OH, —O—CO—$R^{11}$ or —O—CO—O—$R^{11}$ wherein $R^{11}$ is $C_{1-3}$ alkyl, and most preferably —OH.

Preferred compounds of this group are those where A is a group —$(CH_2)_a$—, where a is an integer of 1 to 7, or a group —$(CH_2)_a$—CH=CH—$(CH_2)_b$— where a and b are integers which add up to 0 to 6, more preferably 0 to 5 and most preferably 0 to 4, and analogues of these wherein one or more of the carbon atoms in the these groups are substituted by alkyl, haloalkyl, alkenyl, haloalkenyl or halogen.

A second aspect of the present invention provides the use of a compound of formula (I) as a pesticide; particularly as an insecticide, acaricide and/or fungicide, particularly against mites, whitefly, aphids and/or fungi. Particularly susceptible whitefly include those of Bemisia species. Particularly susceptible aphids include those of Myzus and Aphis species. Particularly susceptible fungi include those of Aspergillus, Pyricularia, Rhizoctonia, Erisiphe and Botrytis species.

A preferred use of this second aspect uses a compound of formula (II) as a pesticide against insects, acarids and/or fungi.

A second preferred use of this second aspect uses a compound of formula (III) as a pesticide against mites, aphids and/or whitefly.

A third preferred use of this second aspect uses a compound of formula (IV) as a pesticide against mites and/or aphids.

In addition to the direct pesticidal activity, ie. direct lethal toxic activity, exhibited by the compounds of formula (I), (II), (III) and (IV), the present inventors have determined that they also exhibit anti-feedant activity on insects of many types, particularly Diabrotica species (Western and Eastern Corn Root Worm), Lepidoptera such as *Spodoptera littoralis* and *Spodoptera frugiperda* and Beetles such as *Phaedon cochleaiae Fab* as well as against those species specified above. Thus the present invention also provides use of compounds of the present invention as pesticides operating as insect and acarid anti-feedants.

A fourth aspect of the present invention provides a method of combating pests, particularly insect, acarid and fungal pests, at a locus which comprises treating the locus with a compound of the general formula (I), preferably being of general formula (II), (III) or (IV).

Preferably, the locus comprises the pests, ie. insects, acarids and/or fungi, per se or environments subject to or subjected to attack by the pests. More preferably, the locus comprises the pests per se, stored food material, plants or animals subject to or subjected to attack by pests, seeds of such plants or the medium in which such plants are growing or are to be grown. Specifically, compounds of formula I may be used in a domestic environment for spraying rooms to combat infestation by houseflies or other insects, acarids or fungi, in a horticultural or agricultural environment for treatment of stored crops, epecially cereals, or to spray growing crops such as cotton or rice to combat infestation by pests, particularly whitefly and related species, and in a medical or veterinary environment, for instance, as a cattle spray to prevent or treat infestation by insects or acarids.

In a fifth aspect the present invention also provides processes for the preparation of compounds of formula (I) and particularly of formula (II), (II) and (IV) as defined above.

Where the compound is one in which m is 0 in formula (I) such method may comprise reacting a compound of the general formula (V)

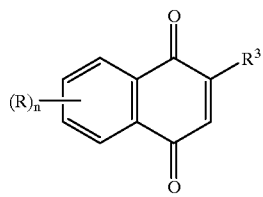

(V)

in which n, R and $R^3$ are as defined above, $R^3$ particularly being —OH, with a compound of the general formula (VI).

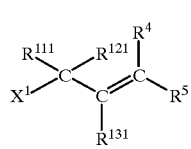

(VI)

in which X represents a leaving group, preferably a hydroxyl group or a halogen, especially a chlorine or bromine, atom; $R^{111}$, $R^{121}$ and $R^{131}$ each independently represent a hydrogen atom or an optionally substituted alkyl group and $R^4$ and $R^5$ are as defined in formula (I), to produce a compound of the general formula (VII)

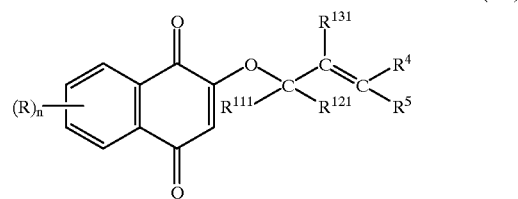

(VII)

in which n, R, $R^{111}$, $R^{121}$, $R^{131,}$ $R^4$ and $R^5$ are as defined above. When X represents a hydroxyl group, the reaction may be carried out under Mitsunobu reaction conditions, that is, using diethyl azodicarboxylate and triphenylphosphine in, for example, tetrahydrofuran at 0° C. When X represents a halogen atom, the reaction may be carried out under alkylating conditions, that is, using a suitable solvent, such as dichloromethane, and a base, such as triethylamine.

The compound of formula (VII) may then be heated in a suitable solvent, preferably an alcohol such as ethanol, to effect a Claisen-type rearrangement resulting in a compound of the general formula (VIII)

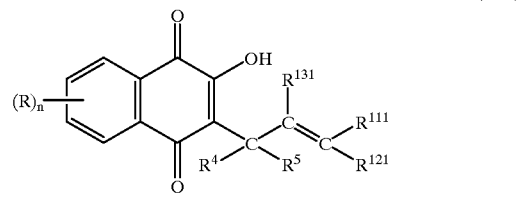

(VIII)

It is also possible to react an alkyl aldehyde directly with the compound of formula (V) in a polar organic solvent under alkaline conditions, eg. with pyrrolidine, and then heat the product under acidic conditions, eg. p-toluenesulphonic acid in a non-polar solvent such as benzene, to effect elimination of water to yield a 3-alkenyl substituted naphthalene ring compound.

Compounds of formula (VIII) correspond to compounds of formula (I), (II) and (IV) in which $R^6$ represents an optionally substituted alkenyl group and may be converted into other compounds of formula (I) by various derivatisation processes.

For instance, compounds of formula I in which $R^6$ represents an optionally substituted alkyl group may be produced by hydrogenation of a suitable compound of formula (VIII), for example, using hydrogen gas with palladium on charcoal as a catalyst. Most compounds of formula (V) are available commercially, but in any case may be prepared from the corresponding 2-hydroxybenzoquinone by, eg. Diels Alder reaction.

In an alternative process for preparing compounds of formula (I), (II), (III) and (IV), which has particular applicability in production of compounds of formula (I) where m is i.e. of formula (III) or (IV), a compound of the general formula (V)

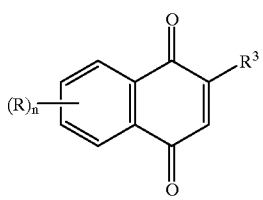

(V)

in which n, R and $R^3$ are as defined above, is reacted with a carboxylic acid $CR_4R_5R_6$—$(A)_m$—COOH where A, m, $R^4$, $R^5$ and $R^6$ are as defined above, in the presence of a free radical initiator, such as ammonium peroxysulphate and silver nitrate in a suitable solvent, such as aqueous acetonitrile, to form a compound of the general formula (I), (II), (III) or (IV).

Compounds of formula (I) obtained in this manner may then be further reacted using the derivatisation processes described above or combinations thereof to obtain further compounds of formula (I), as desired.

For use in this alternative method, in the case where $R^4$ and $R^5$ together with their interjacent carbon atom form a cycloalkyl or cycloalkenyl ring of from 3 to 10 carbons, many of the 1-methylcycloalkyl and cycloalkylenecarboxylic acids are commercially available and the carboxylic acid groups thereon may be extended by known techniques to give access to longer carbon chain lengths, and then substituted if required using techniques well known to those skilled in the art. For example the Arnst-Eistert reaction may be used to give a —$CH_2$— extension (see eg. Meier and Zeller (1975) *Angew. Chem. Int. Ed. Ewgl.,* 14, 32). Alternatively compounds where m is 1 may be accessed by the reaction of the corresponding cycloalkanone with ethyl cyanoacetate and subsquent reaction with a Grignard reagent, followed by hydrolysis to yield the (1'-substituted-cycloalkyl)-acetic acid (see e.g. Amsterdamsky et al (1975) Bull. Soc.Chim.Fr. (3–4 Part 2), p635–643 and Muhs M. A. PhD Thesis, University of Washington, Diss Abst. 14, 765 (1954) to increase the carbon chain length in increments of 1.

For preparation of compounds containing $R^4$ $R^5$ incorporated within rings having higher numbers of carbons, the corresponding monobromo-substituted cycloalkyl or cycloalkenyl compounds may be converted to the carboxylic acids by formation of the Grignard compound using magnesium and then treating this with $C_2$, eg. in the form of dry ice. The carboxylic acid so formed may be converted to the 1-alkyl carboxylate by alkylation using, eg. a compound $R^6$-I, e.g. methyl iodide, in the presence of butyllithium, where $R^6$ is a group as defined above that is stable under these conditions.

For production of 1-fluoro-cycloalkyl/cycloalkenyl carboxylic acids the method of CA 75:17761u may be used wherein buta-1,3-diene is reacted with 1-fluoro- 1-carboxy ethene in the presence of 4-hydroxy-phenol with heating, with subsequent reduction of the ring unsaturation to convert the cycloalkenyl to the cycloalkyl compound. Alternatively the corresponding 2- keto-cycloalkyl-carboxylate compound may be reacted with sodium ethoxide and fluorine gas to give the 1-fluoro-2-keto-cycloalkyl-carboxylate and the keto group may then be reduced using (i) MeSH (ii) Raney Nickel and (iii) potassium hydroxide base (see *J. Org. Chem.* (1983) 48, 724–727 and *J. Org. Chem.* (1982) 47, 3242–3247.

Substitutions, e.g. alkylation, of the cycloalkyucycloalkylene ring at positions in addition to the 1-position to the carboxylate may be accomplished by methods known to those skilled in the art. Starting from the ring mono-unsaturated cycloalkylene carboxylic alkyl esters, alkylation may be directed at the 1-position as previously described and then, using light as initiator, reaction with a compound $R^{20}$—X where $R^{20}$ is alkyl or haloalkyl and X is halogen, eg. a with a compound $CF_3X$, allows introduction of alkyl or haloalkyl groups, eg. $CF_3$- groups. Thereafter reduction using palladium-carbon catalysis conditions allows saturation of the unsaturated bond.

Access to 1-trifluoromethyl cycloalkyl/cycloalkenyl carboxylates may be gained e.g. by reacting the methyl ester of the cycloalkyl/cycloalkenyl-carboxylate with e.g. trifluoromethyl iodide in the presence of LDA, or reacting the 1-keto cycloalkyUcycloalkenyl-carboxylate with trifluoromethyl iodide in the presence of triethylamine followed by reduction. Alternatively 2- trifluoromethyl acrylic acid may be reacted with an optionally substituted buta-1,3-diene with heat in the presence of 4-hydroxyphenol to yield the optionally substituted 1-trifluoromethyl cycloalkenyl carboxylic acid.

Access to compounds where $R^6$ is unsaturated may be obtained through use of the methodology of Wood et al. *J. Chem. Soc Perkin Trans* 1 (1985) 1645–1659 to produce a compound (IX), wherein $R^{141}$ is hydrogen or an optionally substituted alkyl, alkenyl, alkynyl, aryl, alkoxy, alkenoxy, alkynoxy or aryloxy, which compound is reacted with the naphthoquinone under conditions effecting rearrangement as described above. Reduction of such compounds allows access to iso-alkyl groups.

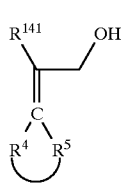

(IX)

In a still further process for preparation of the compounds of the present invention the compound of formula (V) is reacted with a compound of formula X—$(A)_m$—$CR^4R^5R^6$ wherein $R^4$, $R^5$, $R^6$, A and m are as defined for formula I and X is a leaving group that will leave the compound to give a charged radical $^+(A)_m$—$CR^4R^5R^6$; eg. X may be a halogen atom or tosyl group. This reaction is carried out in the presence of an acid, eg. a Lewis acid such as aluminium chloride, using conditions broadly as described by Fieser and Gates (*J. Am. Chem. Soc.* (1941) 63, 2943–2953.

Many other manipulations will occur to those skilled in the art for the purposes of accessing other compounds of the general formula (I).

Compounds of formula (I) in which $R^3$ represents a leaving group as defined above may be prepared by reacting a compound of formula (I) in which $R^3$ represents a hydroxyl group with a compound X-L, where X represents a halogen atom, in the presence of an organic base, preferably a tertiary amine such as triethylarnine, or an inorganic base such as sodium carbonate. For instance compounds of formula I in which $R^3$ represents a group —O—CO—$R^{11}$, where $R^{11}$ is as defined above, may be prepared by acylation of the hydroxy group in a suitable compound of formula V, for instance, by using an acyl chloride $R^{11}$—CO—Cl in a suitable solvent, such as dichloromethane, in the presence of a base, such as triethylarnine. Alternatively compounds of formula I in which $R^3$ represents a hydroxyl group may be reacted with an acid compound HO-L where L is as defined above and includes the acid C=O moiety, in the presence of a dehydrating agent such as dicyclohexylcarbodiimide. A further route to such compounds is provided by reacting a metal salt of a compound of formula (I) in which $R^3$ represents a hydroxyl group, that is, $R^3$ represents a group —OM where M is a metal ion, with a compound X-L as defined above.

Compounds of formula (I) in which $R^1$ with $R^2$ and/or $R^7$ with $R^8$ each independently represent an optionally substituted alkoxy group may be prepared by ketalisation of one or both carbonyl groups in a suitable compound of formula (V) or the corresponding compound of formula (I), for instance, by using a suitable alcohol in basic or acidic conditions, such as by use of a solution of potassium hydroxide in methanol.

Compounds of formula (I) in which $R^1$ with $R^2$ together and/or $R^7$ with $R^8$ together represent a thiocarbonyl group =S may be prepared by treating a suitable compound of formula (I), wherein $R^1$ with $R^2$ and $R^7$ with $R^8$ are both =O, with a thiating agent, such as Lawesson's Reagent (2,4-bis(4-methoxyphenyl)-1,3-dithia-2,4-diphosphetane-2,4-disulphide), using protecting groups where required.

Compounds of formula (I) in which $R^1$ with $R^2$ together and/or $R^7$ with $R^8$ together represent an oxime group =N—OR$^9$, where $R^9$ is as defined above, may be prepared by treating a suitable compound of formula (I), wherein $R^1$ with $R^2$ and $R^7$ with $R^8$ are both =O, with a hydroxylamine or alkoxylamine of formula $R^9$O—NH$_2$, where $R^9$ is as defined above, in the presence of a base, such as pyridine.

Combinations of the above derivatisation processes may be performed to achieve the desired compound of formula (I).

In a sixth aspect of the present invention a composition is provided which comprises a compound of formula (I) and preferably of formula (II), (III) or (IV), as defined above, in association with at least one carrier. Such a composition may contain a single compound or a mixture of several compounds of the present invention. It is also envisaged that different isomers or mixtures of isomers may have different levels or spectra of activity and thus compositions may comprise individual isomers or mixture of isomers.

The compositions of the invention typically contain from 0.001 to 95% by weight of the active ingredient of formula I. Preferably the compositions contain from 0.001 to 25% by weight of the active ingredient when they are in ready-to-use form. However, higher concentrations, for instance, up to 95%, may be present in compositions to be sold as concentrates for dilution before use.

The compositions of the invention may be mixed with a variety of appropriate inert carriers such as solvents, diluents and/or surface-active agents to form dusts, granular solids, wettable powders, mosquito coils or other solid preparations or emulsions, emulsifiable concentrates, sprays, aerosols or other liquid preparations. Suitable solvents and diluents include water, aliphatic and aromatic hydrocarbons such as xylene or other petroleum fractions and alcohols such as ethanol. Surface-active agents may be of an anionic, cationic or non-ionic type. Anti-oxidants or other stabilisers may also be included as well as perfumes and colourings. These inert carriers may be of the type and in proportions such as are conventionally used in pesticidal compositions and thus are conveniently inert with respect to the physiology of a plant to be treated.

Examples of carriers known to be suitable for use in compositions incorporating naphthalene-1,4-diones for pesticidal use include those described in the specifications, and more specifically the Examples, of U.S. Pat. No. 2,572,946, U.S. Pat. No. 4,110,473, U.S. Pat. No. 4,970,328 and JP 90/152943 (the latter to Agro-Kanesho KK).

In addition to these inert carriers, the compositions of the invention may also contain one or more further active ingredients. These further active ingredients may be other compounds which exhibit pesticidal activity and these other compounds may exhibit a synergistic effect with the compounds of the present invention.

The present invention will now be described further by way of illustration only by reference to the following non-limiting Examples and Comparative Examples. Further embodiments of the invention will occur to those skilled in the art in the light of these.

EXAMPLES

Examples 1 to 23 relate to the preparation and properties of compounds of formula (II) forming the first part of the first aspect of the invention; Examples 24 to 34 relate to the preparation and properties of the compounds of formula (III) forming the second part of the first aspect of the invention, and Examples 35 to 50 relate to the preparation and properties of the compounds of formula (IV) forming the third part of the first aspect of the invention together with an example of a compound of formula (II), Example 46, for comparison. Examples 51 to 53 describe production of intermediate compounds of formula (V) where n is 1 or more. Table 14 provides comparative data relating to compounds where the 3-substituent is straight chain alkyl. Starting materials were purchased from Aldrich Chemical Company.

Example 1

Preparation of 2-(1,1-dimethylpropyl)-3-hydroxynaphthalene-1.4-dione (Formula I: n and m =0; $R^1+R^2$ together and $R^7+R^8$ together both represent =O, $R^3$=—OH; —CR$^4$R$^5$—=—C(CH$_3$)$_2$—; $R^6$ =—C$_2$H$_5$)

(a) Preparation of 2-(3-methylbut-2-enyloxy)-naphthalene-1,4-dione

To a stirred solution of 2-hydroxynaphthalene-1,4-dione (10.0 g, 57.4 mmol) and triphenylphosphine (15.1 g, 57.4 mmol) in dry tetrahydrofuran (150 ml) at 0° C. under an atmosphere of nitrogen was added diethyl azodicarboxylate (10.0 g, 57.4 mmol). After stirring for a further 5 minutes, a solution of 3-methylbut-2-enol (7.42 g, 86.1 mmol) in dry tetrahydrofuran (10 ml) was added dropwise and stirring was continued for 2 hours. The precipitate was collected, air-dried and recrystallised from aqueous methanol to yield 2-(3-methylbut-2-enyloxy)naphthalene-1,4-dione (8.3 g) as a yellow crystalline solid, m.pt.: 138° C.

(b) Preparation of 2-(1,1-dimethylprop-2-enyl)-3-hydroxy-naphthalene-1.4-dione

A solution of 2-(3-methylbut-2-enyloxy)naphthalene-1,4-dione (4.27 g, 24.8 mmol) obtained in (a) above in absolute ethanol (125 ml) was refluxed for 6 hours. The mixture was cooled and the solvent removed in vacuo. The residue was dissolved in diethyl ether and extracted with 1% (w/v) aqueous sodium hydroxide solution (6×25 ml). The combined basic fractions were acidified to pH 5 with 2M hydrochloric acid and extracted with diethyl ether (6×25 ml). The combined ethereal extracts were washed successively with water (2×25 ml), saturated aqueous sodium chloride solution (25 ml) and dried over anhydrous magnesium sulphate. Filtration and evaporation of the solvent under reduced pressure followed by recrystallisation from aqueous methanol, yielded 2-(1,1-dimethylprop-2-enyl)-3- hydroxynaphthalene-1,4-dione (4.27 g) as a yellow crystalline solid, m.pt.: 60° C.

(c) Preparation of 2-(1,1-dimethylpropyl)-3-hydroxy-naphthalene-1,4-dione

A mixture of 2-(1,1-dimethylprop-2-enyl)-3-hydroxynaphthalene-1,4-dione (2.00 g, 8.3 mmol) obtained in (b) above and 10% palladium on charcoal (50 mg) in absolute ethanol (30 ml) was stirred under an atmosphere of hydrogen (balloon) at room temperature (about 20° C.) for 1 hour. The mixture was filtered through "CELITE" (Registered Trade Mark) (acid washed, approx. 95% $SiO_2$) and the solvent evaporated under reduced pressure. The residue was recrystallised from methanol-petrol to yield 2-(1,1-dimethylpropyl)-3-hydroxynaphthalene-1,4-dione (1.98 g) as a yellow crystalline solid, m.pt.: 52° C.

Example 2

Preparation of 2-(1,1-dimethylpropyl)-3-ethanoyloxy-naphthalene-1,4-dione (Formula I: n and m=0; $R^1$+$R^2$ together and $R^7$+$R^8$ together both represent =O; $R^3$=—O—CO—$CH_3$;—$CR^4R^5$—=—C($CH_3$)$_2$—;$R^6$=—$C_2H_5$)

To a stirred solution of 2-(1,1-dimethylpropyl)-3-hydroxynaphthalene-1,4-dione (2.00 g, 8.2 mmol) obtained as in Example 1 above in dry dichloromethane (20 ml) at 0° C. was sequentially added pyridine (0.5 ml) and ethanoyl chloride (2.59 g). The mixture was then stirred for 30 minutes before diluting with diethyl ether, washing with water, saturated sodium hydrogen carbonate solution and saturated sodium chloride solution and drying over magnesium sulphate. Filtration and evaporation of the solvents under reduced pressure followed by silica gel column chromatography yielded 2-(1,1-dimethylpropyl)-3-ethanoyloxynaphthalene-1,4-dione (2.06 g) as a yellow crystalline solid, m.pt.: 53° C.

Example 3

Preparation of 2-(t-butyl)-3-hydroxy-naphthalene-1,4-dione (Formula I: n and m=0; $R^1$+$R^2$ together and $R^7$ and $R^8$ together both represent =O; $R^3$=—OH; —$CR^4R^5$—=—C($CH_3$)$_2$—; $R^6$=—$CH_3$)

2-Hydroxynaphthalene-1,4-dione (1.00 g, 5.68 mmol), pivalic acid (870 mg, 8.51 mmol) and silver nitrate (568 mg) were heated in a mixture of acetonitrile (20 ml) and water (20 ml) at 60–65° C. A solution of animonium peroxysulphate (1.94 g, 8.51 mmol) in water (10 ml) was added dropwise and the mixture heated for 1 hour. The mixture was then cooled to room temperature (about 20° C.), diluted with diethyl ether and extracted with 1% (w/v) aqueous sodium hydroxide solution (4×25 ml). The combined aqueous layers were then acidified with 2M hydrochloric acid and extracted with diethyl ether (3×25 ml). The combined ethereal extracts were then washed with water and saturated sodium chloride solution and dried over magnesium sulphate. Filtration and evaporation of the solvent under reduced pressure and purification by silica gel column chromatography yielded 2-(t-butyl)-3-hydroxynaphthalene-1,4-dione (450 mg) as a yellow crystalline solid, m.pt.: 89° C.

Examples 4 to 11 and 13

By processes similar to those described in Examples 1 and 2 above, further compounds according to the invention were prepared as detailed in the Table I below. In this table, the compounds are identified by reference to formula I.

Example 12

Preparation of 2-(1,1-dimethylprop-2-enyl)-3-methoxy-naphthalene-1,4-dione (Formula I: n and m=0; $R^1$+$R^2$ together and $R^7$+$R^8$ together both represent =O, $R^3$=—$OCH_3$; m is 0; —$CR^4R^5$—=—C($CH_3$)$_2$—;$R^6$=—CH=$CH_2$)

To a stirred solution of 2-(1,1-dimethylprop-2-enyl)-3-hydroxy-naphthalene-1,4-dione (50 mg, 0.21 mmol) in ether (5 ml) at 0° C. under nitrogen was added an ethereal solution of diazomethane (2 ml). After 2 hours the solvent was removed under reduced pressure and the residue purified by silica gel column chromatography to yield the title compound (47 mg).

Example 14

Preparation of 1,1-dimethoxy-2-(1,1-dimethylprop-2-enyl)-3-hydroxynaphthalene-1.4-dione (a) 2-(1,1-dimethylprop-2-enyl)-3-acetyloxy-naphthalene-1,4-dione The standard acetylation procedure of Example 2 was repeated on compound 1(b) (1.00 g, 4.13 mmol) to give the title compound.

(b) 1,1-dimethoxy-2-hydroxy-3-(1,1-dimethylprop-2-enyl)-naphthalene-4-one.

To a stirred solution of compound 14(a) (750 mg, 2.63 mmol) in methanol (30 ml) and THF (5 ml) was added an aqueous solution of potassium hydroxide (1.0 g) in water (10 ml). The mixture was stirred for 1 hour before reducing to half volume and diluting with water (20 ml) and then the aqueous mixture was extracted with ether (3×20 ml). The combined ether fractions were washed successively with water (2×20 ml), saturated sodium carbonate solution (3×20 ml), water (2×20 ml), saturated sodium chloride solution (20 ml) and dried over magnesium sulphate. Filtration and evaporation as solvent under reduced pressure and silica gel column chromatography yielded the title compound (173 mg).

Example 15

Preparation of 2-(1,1-dimethylprop-2-enyl)-2-hydroxy-1-methoxyimino-naphthalene-4-one A solution of the product of Example 1 (b) (250 mg, 1.03 mmol) and methoxyamine hydrochloride (95 mg, 1.14 mmol) in pyridine (5 ml) was stirred for 48 hours. The reaction mixture was dissolved in ether (50 ml) and washed with water (2×10 ml), 2M hydrochloric acid (2×10 ml), water (2×10 ml), saturated sodium chloride solution (10 ml) and dried over magnesium sulphate. Filtration and evaporation of the solvent under reduced pressure and silica gel chromatography yielded the title compound (56 mg).

TABLE 1

In all the following examples n and m = O, $R^4 = R^5 = CH_3$ and $R^7$ and $R^8$ together represent =O

| Example No. | $R^1$ | $R^2$ | $R^3$ | $R^6$ | M.pt (°C.) | $n_D$ |
|---|---|---|---|---|---|---|
| 4 | =O | | —O—CO—$C_2H_5$ | —CH=$CH_2$ | | 1.5621 |
| 5 | " | | —O—CO—$^nC_3H_7$ | " | | 1.5560 |
| 6 | " | | —O—CO—$^nC_4H_9$ | " | | 1.5436 |
| 7 | " | | —O—CO—$^nC_5H_{11}$ | " | | 1.6532 |
| 8 | " | | —O—CO—$^nC_9H_{19}$ | " | | 1.6532 |
| 9 | " | | —O—CO—$CH_2F$ | " | | 1.5429 |
| 10 | " | | —O—CO—$CH(CH_3)_2$ | " | | 1.5390 |
| 11 | " | | —O—CO—$C_6H_5$ | " | 88–90 | |
| 12 | =O | | —$OCH_3$ | —CH=$CH_2$ | 65 | |
| 13 | " | | —O—$CH_2C_6H_5$ | " | | 1.6042 |
| 14 | —$OCH_3$ | —$OCH_3$ | —OH | " | 67 | |
| 15 | =N—$OCH_3$ | | " | " | 114–115 | |
| 16 | =O | | " | —$^nC_3H_7$ | | |
| 17 | " | | —O—CO—$C_2H_5$ | —$^nC_3H_7$ | | |
| 18 | " | | —OH | —$^nC_5H_{11}$ | | |

NB $^nD$ signifies refractive index at the sodium D lines.

Example 19

Pesticidal Activity

Pesticidal activity was assessed against houseflies, mustard beetles, diamond-back moths (larvae), mites and whitefly using the following methods.

Houseflies (MD) (*Musca domestica*)

Female flies were treated on the thorax with a one microlitre drop of test compound dissolved in acetone. Two replicates of 15 flies were used at each dose rate and 6 dose rates were used per compound under test. After treatment, the flies were maintained at a temperature of 20°±1° C. and kill was assessed 24 and 48 hours after treatment. $LD_{50}$ values were calculated in micrograms of test compound per fly (see Sawicki et al., Bulletin of the World Health Organisation, 35, 893 (1966) and Sawicki et al., Entomologia and Exp. Appli 10, 253, (1967).

Mustard beetles (PC) (*Phaedon cochleariae Fab*)

A one microlitre drop of an acetone solution of the test compound was applied ventrally to adult mustard beetles using a micro drop applicator. The treated insects were maintained for 48 hours after which time kill was assessed. Two replicates each of 20 to 25 mustard beetles were used at each dose level and 5 dose levels were treated comparably. $LD_{50}$ values were calculated as for houseflies.

Diamond-back moth (PX) (*Plutella xylostella*)

Fifth instar larvae were treated with a 0.5 μl drop of test compound in acetone. Three replicates of 10 larvae each were used at each dose rate and 5 dose rates were used per compound under test. After treatment, the larvae were maintained at about 22° C., and kill was assessed as failure to pupate 5 days later. $LD_{50}$ values were calculated as for houseflies.

Mites (TU) (*Tetranychus urticae*)

25 adult female mites were immersed in 35 μl of a solution of the test compound in a 1:4 acetone-water mixture for 30 seconds. The treated insects were maintained at 21°±2° C. and kill was assessed 72 hours after treatment. Mites exhibiting repetitive (non-reflex) movement of more than one locomotory appendage after this period were recorded as alive. Three replicates of 25 mites each were used at each dose rate and 5 or 6 dose rates were used per compound under test. $LC_{50}$ values were calculated in ppm of the solution of the test compound per insect. The test was carried out using a susceptible strain of mites (GSS) supplied by Schering, AG, Berlin.

Whitefly (BT) (*Bemisia tabaci*)

Acetone solutions (0.100 ml) of the test compounds were placed in 10 ml glass vials and evaporated with rotation to deposit a film of the compound. Thirty adult whiteflies were placed inside the vial, then after 60 minutes, the treated insects were transferred onto untreated cotton leaf discs which were kept moist on a bed of agar gel. The temperature was maintained at 25° C. and mortality assessed after 48 hours. Three replicates were used at each of 5 to 7 dose levels per compound. $LC_{50}$ values (ppm solution) were calculated by using a computer software package ("Polo-PC available from LeOra Software, Berkeley, Calif.) (See M. R. Cahill and B. Hackett in Proceedings Brighton Crop Protection Conference, 1992). The test was carried out using a susceptible strain of whitefly (SUD-S) which was collected in Sudan in 1978 from cotton.

The results of these tests are set out in Table 2 below. The values given are in $LD_{50}$ (μg/insect) and $LC_{50}$ (ppm solution of test compound) unless otherwise stated.

In all the tables set out in this specification lack of detectable activity is indicated by 'NA' and the absence of test data by '-'.

TABLE 2

| Compound Example No. | MD ($LD_{50}$) | PC ($LD_{50}$) | PX ($LD_{50}$) | TU (GSS) ($LC_{50}$) | BT (SUD-S) ($LC_{50}$) |
|---|---|---|---|---|---|
| 1 | <10 | c. 10 | — | 39 | 19 |
| 2 | <10 | c. 6.0 | c. 10 | 64 | 4.8 |
| 3 | c. 2.5 | c. 6.0 | c. 8.0 | 81 | 8 |
| 4 | 8.2 | 3.9 | — | 18 | 5.3 |
| 5 | — | 6.9 | — | 84 | 13 |
| 6 | c. 2.0 | 2.1 | — | 27 | 16 |
| 7 | >20 | c. 6.0 | — | 53 | <100 |
| 8 | — | c. 8.0 | c. 0.1 | 630 | — |
| 9 | — | 0.41 | — | 140 | 13.4 |
| 10 | >20 | c. 6.0 | — | 15 | 35 |
| 11 | — | — | — | c. 50 | — |
| 12 | >20 | c. 12.0 | — | — | — |
| 13 | >20 | >20 | c. 8.0 | >1000 | >1000 |
| 14 | c. 2.5 | c. 6.0 | — | c. 800 | — |
| 15 | — | 35%* | — | — | 97%** |
| 16 | 8.8 | c. 10 | — | 91 | 10 |
| 17 | 14 | NA | — | 50 | — |

TABLE 2-continued

| Compound Example No. | MD (LD$_{50}$) | PC (LD$_{50}$) | PX (LD$_{50}$) | TU (GSS) (LC$_{50}$) | BT (SUD-S) (LC$_{50}$) |
|---|---|---|---|---|---|
| 18 | 13 | c. 15 | — | c 100 | 10 |
| A | >>20 | 0.36 | — | 64 | 82 |

*% Kill at 20 μg/insect (LD$_{50}$)
**% Kill at 1000 ppm solution of test compound
Compound A = Example 1, page 5 of DE 2641343 A1 which is 2-n-dodecyl-3-ethanoyloxynaphthalene-1,4-dione (Formula I: n and m = 0; $R^1 + R^2$ together and $R^7 + R^8$ together are both = O; $R^3$ = —O—CO—CH$_3$; $R^4 = R^5$ = H; $R^6 = {}^nC_{11}H_{23}$)

Example 20

Activity against resistant mites (TU) (*Tetranychus urticae*)

The test of Example 16 (TU(GSS)) was repeated using a strain of mites which is resistant to bifenthrin (NYR-Bif-1000). The NYR-Bif-1000 strain was provided by the Department of Entomology, Cornell University, New York.

The results of this test are set out in Table 3 below. The values given are LC$_{50}$ (ppm solution of test compound).

TABLE 3

| Compound of Example No. | TU (NYR-Bif-1000) (LC$_{50}$) |
|---|---|
| 1 | 84 ppm |
| 2 | 83 ppm |

Example 21

Activity against resistant whitefly (BT) (*Bemisia tabaci*)

The test of Example 16 (BT (SUD-S)) was repeated using a resistant strain of whitefly (Ned 7). The Ned 7 strain was collected in the Netherlands in April, 1993 from hibiscus by J. Fransen and is highly resistant to organophosphate and carbamate insecticides and the insect growth regulator buprofezin.

The results of this test are set out in Table 4 below. The values given are LC$_{50}$ (ppm solution of test compound).

TABLE 4

| Compound of Example No. | BT (Ned 7) (LC$_{50}$) |
|---|---|
| 5 | 21 |
| A | 470 |

Further tests with various resistant strains of whitefly have shown that the compounds of Examples 1 to 15 are highly active against resistant strains.

Example 22

Aphicidal activity

Activity against resistant (R) and susceptible (S) strains of aphid (*Myzus persicae*) was assessed using the following method.

Entrapment rings of fluon were painted halfway up the inside of 4 cm lengths of glass tubing (1.5 cm diameter), and squares of insect-proof gauze were attached to one end of each tube by elastic bands. Fifteen apterous adults were then gently transferred into the tubes using a sable-hair brush, and the tube sealed with a second gauze square.

Tubes containing aphids were dipped into insecticide solutions for 10 seconds, dried on blotting paper, and then inverted and tapped to cause treated aphids to fall to the unimmersed end of each tube. Handling mortality (usually zero or very slight) was scored after 1 hour, when aphids were transferred onto chinese cabbage leaf-discs (35 mm diameter) on an agar bed (25 mm in depth) in disposible plastic containers (30 mm high) and confined by applying a ring of fluon to the exposed lip of the container. Containers were store upright, without lids, in a constant environment facility maintained at 25° C. under continuous room lighting. Mortality was assessed at 24, 48 and 72 hours. Two replicates of 15 aphids each were used at each dose rate and 5 or 6 dose rates were used per compound under test.

The test was carried out using a susceptible strain of aphids (US1L) collected in the field in East Anglia, UK and an extremely resistant strain of aphids (794Jz) (R3 esterase, sensitive AChE) collected from glasshouses in the UK.

The results of this test are set out in Table 5 below. The values given are % mortality corrected for control data. The control comprised the test solution without active ingredient.

Further tests using the susceptible strain of *Aphis gossipii* 81–171B were also carried out and results indiocate useful activity, particularly with compounds of formula (IV).

TABLE 5

| COMPOUND OF EXAMPLE NO. | | CONCENTRATION OF ACTIVE INGREDIENT | | | CONTROL MORTALITY |
|---|---|---|---|---|---|
| | | 250 PPM | 100 PPM | 40 PPM | |
| 1 | S | 26 | 11 | 00 | 10 |
|   | R | 43 | 10 | 03 | 00 |
| 2 | S | 27 | 03 | 20 | 00 |
|   | R | 47 | 17 | 00 | 00 |
| 3 | S | 87 | 27 | 04 | 00 |
|   | R | 87 | 13 | 10 | 00 |

Example 23

Fungicidal Activity

Fungitoxicity of coded compounds to isolates of *Aspergillus niger*, *Pyricularia oryzae* (=*Magnaporthe grisea*) and *Rhizoctonia solani* was tested in vitro.

Each compound was incorporated into potato dextrose agar in solvent (50/50 ethanol/acetone) at 0.5 ml solvent per 250 ml agar while the autoclaved agar was still molten and cooled to 50° C. Each compound was tested at a single concentration (100 mg l$^{-1}$).

Each test, usually of two compounds, included three control treatments: (i) a standard fungicide (carbendazim at 1 or 5 mg l$^{-1}$ or prochloraz at 1 mg l$^{-1}$); (ii) ethanol/acetone only; and (iii) no additions. The fungicides used as standards may be considered as representative of active, commercially available compounds.

Each fungus was tested on agar in four Petri dishes per treatment, with three replicate fungal colonies per plate (one colony for *R. solani*). *A. niger* and *R. solani* were incubated for 4 days at 20–25° C., and *P. oryzae* for 7 days. Increase in colony diameter was then measured and used to determine activity:

The results of these tests are set out in Table 6 below. The values given are % inhibition of growth in colony diameter in agar plates.

TABLE 6

| Compound of Example No. | Fungus | Activity at 100 mg l$^{-1}$ | Activity at 5 mg l$^{-1}$ | Activity at 1 mg l$^{-1}$ |
|---|---|---|---|---|
| 1 | A. niger | 63 | | |
| 2 | A. niger | 38 | | |
| 3 | A. niger | 61 | | |
| 1 | P. oryzae | 100 | | |
| 2 | P. oryzae | 89 | | |
| 3 | P. oryzae | 100 | | |
| 1 | R. solani | 95 | | |
| 2 | R. solani | 81 | | |
| 3 | R. solani | 92 | | |
| Prochloraz | A. niger | | | 97.8 |
| Carbendazim | P. oryzae | | 99.8 | 14.7 |
| Carbendazim | R. solani | | 82.4 | 3.3 |

In addition, tests have shown that the compounds of formula I exhibit good fungicidal activity against a broad spectrum of fungi which cause diseases in both cereal and broad leaved crops. Particularly, good activity has been observed against fungi of the genera Erysiphe, especially *Erysiphe graminis*, and Botrytis, especially *Botrytis fabae* and *Botrytis cinerea*, as well as the genera Rhizoctonia, Pyricularia and Aspergillus as illustraded above.

Example 24

Preparation of 2-hydroxy-3-(1'-methylcyclopentyl)-naphthalene-1,4-dione (Formula III: n=0; m=0; R$^1$+R$^2$ together and R$^7$+R$^8$ together both represent =O; R$^3$=—OH; —CR$^4$R$^5$—=cyclopentyl; R$^6$=—CH$_3$)

To a stirred solution of diisopropylamine (3.95 g, 39.0 mmol) in dry THF (50 ml) at −78° C. under an atmosphere of nitrogen was added n- butyllithium (2.5M, 11.7 ml, 29.3 mmol). The mixture was stirred for 10 minutes before methyl cyclopentanecarboxylate (Aldrich) (2.5 g, 19.5 mmol) was added dropwise. Stirring was continued for a further 10 minutes before methyl iodide (8.31 g, 58.5 mmol) was added dropwise. The reaction mixture was stirred at −78° C. for a further 1 hour before being allowed to warm up to room temperature and being stirred for a further 1 hour. The reaction mixture was poured onto an admixture of water and ether (1:1, 100 ml) and acidified with dilute hydrochloric acid (2M). The aqueous solution was separated and extracted further with ether (3×25 ml) and the combined ether layers were washed with water (2×50 ml), saturated sodium chloride solution (50 ml) and dried over MgSO$_4$. Filtration and evaporation of solvent under reduced pressure yielded methyl 1-methylcyclopentanecarboxylate as a colourless oil (2.38 g, b.p. 106° C. at 10 mmHg[Kugelrohr]).

A solution of the methyl ester (2.30 g) and potassium hydroxide (5.00 g) in a mixture of ethylene glycol (40 ml) and water (10 ml) was refluxed for 16 hours and then cooled to room temperature before being diluted with ether, the aqueous layer separated, 15 acidified with dilute hydrochloric acid (2M) and extracted with ether (2×25 ml). The combined ether layers were washed with water (2×25 ml) and then saturated sodium chloride solution (25 ml) and dried over MgSO$_4$. Filtration and evaporation yielded 1-methylcyclopentanecarboxylic acid (1.69 g).

A 50% excess of this acid was added to a stirred solution of 2-hydroxynaphthalene-1,4-dione (1.00 g, 5.7 mmol), and silver nitrate (600 mg) in a mixture of acetonitrile (20 ml) and water (20 ml) at 65° C. and a solution of ammonium peroxysulphate (1.96 g, 8.6 mmol) in water (10 ml) was slowly added to that over a period of 15 minutes. The mixture was heated for a further hour before cooling to room temperature (about 20° C.) and diluting with diethyl ether (50 ml). The organic phase was separated and washed successively with 25 water, dilute aqueous sodium hydrogen carbonate solution, water and saturated sodium chloride solution before drying over magnesium sulphate as set out in Example 3. Filtration and evaporation of the solvent under reduced pressure followed by silica gel column chromatography using 2:1 petrol:diethyl ether as eluant gave 2-hydroxy-3-(1-methylcyclopentyl)naphthalene-1,4-dione (mp 116–118° C.).

Example 25

Preparation of 2-hydroxy-3-(1'-methylcyclohexyl)-naphthalene-4-dione (Formula III: n=0; m=0; R$^1$+R$^2$ together and R$^7$+R$^8$ together both represent =O; R$^3$=—OH; —CR$^4$R$^5$—=cyclohexyl; R$^6$=—CH$_3$)

To a stirred solution of 2-hydroxy-naphthalene-1,4-dione (1.00 g, 5.7 mmol), 1-methylcyclohexanecarboxylic acid (1.22 g, 8.6 mmol) and silver nitrate (600 mg) in a mixture of acetonitrile (20 ml) and water (20 ml) at 65° C. was slowly added a solution of ammonium peroxysulphate (1.96 g, 8.6 mmol) in water (10 ml) over a period of 15 minutes. The mixture was heated for a further hour before cooling to room temperature (about 20° C.) and diluting with diethyl ether (50 ml). The organic phase was separated and washed successively with water, dilute aqueous sodium hydrogen carbonate solution, water and saturated sodium chloride solution before drying over magnesium sulphate. Filtration and evaporation of the solvent under reduced pressure followed by silica gel column chromatography using 2:1 petrol:diethyl ether as eluant gave 2-hydroxy-3-(1-methylcyclohexyl)naphthalene-1,4-dione (296 mg) as a yellow crystalline compound, m.pt.: 79° C.

Example 26

Preparation of 2-(1'-ethylcyclohexyl)-3-hydroxy-naphthalene-1,4-dione

The title compound was prepared by hydrogenation of the compound of Example 27, provided as set out below, using Pd/C catalyst in ethanol (mp 56° C.) using the method of Example 1c.

Example 27

Preparation of 2-(1'-ethenecyclohexyl)-3-hydroxy-naphthalene-1,4-dione (Formula III: n=0; m=0; R$^1$+R$^2$ together and R$^7$+R$^8$ together both represent =O; R$^3$=—OH; —CR$^4$R$^5$—=cyclohexyl; R$^6$=—CH=CH$_2$)

To a stirred solution of ethyl cyclohexylideneacetate (see route to this by Wadsworth and Emmons in Org. Synth. Coll. Vol 5 547) (3.00 g, 17.8 mmol) in dry ether (50 ml) under an atmosphere of nitrogen at 0° C. was added lithium aluminium hydride (407 mg, 10.7 mol) portionwise and the mixture stirred for 2 hours before quenching with dilute hydrochloric acid (2M; 20 ml). The mixture was filtered and the aqueous layer was separated and extracted further with ether (2×25 ml) and the combined ether layers washed with water (2×25 ml) and saturated sodium chloride solution (25 ml) and then dried over MgSO$_4$. Filtration and evaporation of the solvent and distillation of the residue gave 2-cyclohexylidene ethanol (2.16 g, bp. 112° C. at 10 mmHg [Kugelrohr]).

To a stirred solution of 2-hydroxy-naphthalene-1,4-dione (2.50 g, 14.4 mmol) and triphenylphosphine (3.79 g, 14.4 mmol) in dry THF (50 ml) under nitrogen was added dropwise a solution of diethyl azodicarboxylate (2.50 g, 14.4 mmol) in THF (2 ml). The mixture was stirred for 5 minutes before the cyclohexylidene ethanol (2.00 g, 15.8 mmol) in THF (2 ml) was added dropwise. The mixture was stirred for 2 hours allowing the temperature to rise to room temperature and then diluted with ether (100 ml) and washed with 1% sodium hydroxide solution (5×25 ml), water (2×25 ml) and saturated sodium chloride solution (25 ml) and dried over MgSO$_4$. Filtration and evaporation of the solvent yielded a brown residue which was dissolved in ethanol (50 ml) and refluxed for 6 hours.

The mixture was cooled, concentrated to half its volume and diluted with ether (100 ml). The etherial solution was extracted with 1% sodium hydroxide solution (6×25 ml) and the combined basic fractions were acidified (2M hydrochloric acid) and extracted with ether (6×25 ml) with combined ether layers being washed with water (2×25 ml) and saturated sodium chloride solution (25 ml) and dried over MgSO$_4$. Filtration and evaporation of the solvent and purification by silica gel column chromatography yielded the title compound as a yellow crystalline compound (153 mg; mp 112–113° C.).

Example 28

Preparation of 2-hydroxy-3-(1'-trifluoromethylcyclohexyl)-naphthalene-1,4-dione
(Formula III: n=0; m=0; R$^1$+R$^2$ together and R$^7$+R$^8$ together both represent =O; R$^3$=—OH; —CR$^4$R$^5$—=cyclohexyl; R$^6$=—CF$_3$).

Trifluoromethylacrylic acid (1.5 g: 10.7 mmol), butadiene sulphone (1.27 g: 10.7 mmol) and hydroxyquinone (15 mg) were heated at 160° C. in a pressure vessel bomb (pressure approx. 3 bar at completion) for two and a half hours. The mixture was then cooled and dissolved in diethyl ether and extracted with 2M sodium hydroxide (3×25 ml). The combined basic fractions were acidified with 2M HCl and extracted with diethyl ether (5×25 ml). The combined ether fractions were washed with water then saturated sodium chloride solution before drying over magnesium sulphate, filtering and evaporation of sovent to yield a brownish solid (1.267 g). The crude product was purified on a silica column using 1:1 petroleum ether/diethyl ether eluant yielding 927 mg of the product 1-trifluoromethyl-cyclohexyl-3-enecarboxylic acid. This compound was hydrogenated by the method of Example 1(c) to give 1-trifluoromethylcyclohexanecarboxylic acid.

2-benzoyloxy-naphthalene-1,4-dione (355 mg: 1.27 mmol), 1-trifluoromethyl-cyclohexane carboxylic acid (250 mg: 1.27 mmol) and silver nitrate (108 mg: 0.64 mmol) were heated in acetonitrile (5 ml) and water (3 ml) at 65–70° C. A solution of ammonium peroxysulphate (436 mg: 1.91 mmol) in water (1 ml) was added dropwise and the mixture heated for 1 hour. The reaction mixture was cooled, diluted with water (20 ml) and extracted with ether (3×20 ml). The combined ether layers were dried over magnesium sulphate and evaporated to dryness.

The resultant ester was hydrolysed by dissolving in a mixture of THF (20 ml) and 2M aqueous KOH (10 ml) and stirring at room temperature for 2 hours. The mixture was diluted with water (20 ml), washed with ether (2×20 ml), acidified with 2M HCl and extracted with ether (3×20 ml). The combined ether extracts were washed with water, dried over magnesium sulphate and the solvent evaporated under reduced pressure. The residue was purified by silica gel column chromatography to give the product (mp 114° C.).

Example 29

Preparation of 2-hydroxy-3-(1'-methylcycloheptyl)-naphthalene-1,4-dione.

(Formula III: n=0; m=0; R$^1$+R$^2$ together and R$^7$+R$^8$ together both represent =O; R$^3$=—OH; —CR$^4$R$^5$—=cycloheptl; R$^6$=—CH$_3$)

To a stirred solution of diisopropylamine (7.47 g, 73.8 mmol) in dry THF at −78° C. under nitrogen was added n-butyllithium(2.5M, 29.5 ml, 73 8 mmol). The mixture was stirred for 10 minutes before cycloheptanecarboxylic acid (2.10 g, 14.8 mmol) was added dropwise and the reaction stirred at −78° C. for a further 10 minutes before refluxing for a further 2 hours. The reaction was cooled to 0° C. and methyl iodide (5.76 g, 40.6 ml) was added dropwise before refluxing for a further 1 hour before cooling to room temperature. The reaction mixture was poured onto an admixture of water/ether (100 ml/SO ml) and the aqueous layer was separated, acidified with dilute hydrochloric acid (2M) and extracted with ether (5×25 ml). The combined ether layers were washed with water (2×50 ml) and saturated sodium chloride solution (50 ml) before being dried over MgSO$_4$. Filtration and evaporation of solvent under reduced pressure yielded the 1-methylcycloheptanecarboxylic acid which was recrystallised from hexane (2.20 g, mp 46° C.). The title compound was produced by the method of Example 24 using this acid in place of the 1-methylcyclopentanecarboxylic acid.

Examples 30 and 31

Further compounds of the second group of the first aspect of the invention were synthesized by similar methods to those of Examples 24 to 29 and are referred to in the Tables 9 and 10 below as Examples 30 to 31 where physical and activity data are set out.

Example 33

Preparation of 2-acetoxy-3-((1'-methylcyclohexyl)-methyl)-naphthalene-4-dione

To a stirred solution of 2-acetoxy-naphthalne-1,4-dione (1.12 g; 5.18 mmol), (1-methylcyclohexyl)acetic acid (prepared by the procedure of Amsterdarnsky et al *Bull. Soc. Chim. Fr* (1975) 3–4 part 2, 635–643) (850 mg; 5.44 mmol) and silver nitrate (520 mg) in acetonitrile (15 ml) and water (20 ml) heated at 65–70° C. was added an aqueous solution of ammonium persulphate (1.77 g, 7.77 mmol) in water (10 ml). After heating for 1 hour the mixture was cooled, diluted with water (50 ml) and extracted with ether (3×40 ml). The combined ether fractions were washed with water (3×25 ml), saturated sodium chloride solution (25 ml) and dried over magnesium sulphate. Filtration and evaporation of solvents under reduced pressure and silica gel chromatography yielded the title compound as a yellow solid (736 mg).

Examples 32 and 34

Preparation of 2-hydroxy-3-((1'methylcyclohexyl)-methyl)-naphthalene-1.4-dione (Example 32) and 1.1-dimethoxy-2-hydroxy-3-((1'-methylcyclohexyl)-methyl)-naphthalene-1,4-dione (Example 34)

To a stirred solution of compound of Example 33 (750 mg; 2.3 mmol) in an admixture of THF/methanol (1:1; 30 ml) was added an aqueous solution of potassium hydroxide (6.45 mg; 1.5 mmol) in water (8 ml) at room temperature and the reaction stirred for 2 hours. The mixture was diluted with water (100 ml), washed with ether (20 ml), acidified with 2M hydrochloric acid and extracted with ether (3×25 ml). The combined ether layers were washed with water (2×20 ml), saturated sodium chloride solution (20 ml) and dried over magnesium sulphate. Filtration and evaporation of the solvent under reduced pressure and silica gel column chromatography gave the compounds of Example 32 and 34 in two bands.

TABLE 8

| COMPOUND EXAMPLE NO. | Aphid Strain | CONCENTRATION OF ACTIVE INGREDIENT | | | CONTROL MORT-ALITY |
|---|---|---|---|---|---|
| | | 250 PPM | 100 PPM | 40 PPM | |
| 25 | S | 67 | 23 | 07 | 0 |
| | R | 79 | 27 | 10 | 0 |

TABLE 9

Compounds are of Formula III wherein $R^1$ with $R^2$ is =O $R^7$ with $R^8$ is =O unless otherwise stated; n = 0 and m = 1

| Compound of Example No. | $R^3$ | m | A | $R^4$ | $R^5$ | $R^6$ | Other | mp |
|---|---|---|---|---|---|---|---|---|
| 24 | —OH | 0 | — | cyclopentyl | | —$CH_3$ | | 117–118° C. |
| 25 | —OH | 0 | — | cyclohexyl | | —$CH_3$ | | 79° C. |
| 26 | —OH | 0 | — | cyclohexyl | | —$CH_2$—$CH_3$ | | 56° C. |
| 27 | —OH | 0 | — | cyclohexyl | | —CH=$CH_2$ | | 112–113° C. |
| 28 | —OH | 0 | — | cyclohexyl | | —$CF_3$ | | 114° C. |
| 29 | —OH | 0 | — | cycloheptyl | | —$CH_3$ | | 68° C. |
| 30 | —OH | 0 | — | cyclopentyl | | —CH=$CH_2$ | | 92–94° C. |
| 31 | —OH | 0 | — | cyclohex-2-enyl | | —$CH_3$ | | 89–90° C. |
| 32 | —OH | 1 | —$CH_2$— | cyclohexyl | | —$CH_3$ | | 114° C. |
| 33 | —OAc | 1 | —$CH_2$— | cyclohexyl | | —$CH_3$ | | 114° C. |
| 34 | —OH | 1 | —$CH_2$— | cyclohexyl | | —$CH_3$ | R1, R2 = OMe | 136–138° C. |

Pesticidal activity was assessed against houseflies, mustard beetles, mites, aphids and whitefly using the methods of Examples 19 to 22. All strains were susceptible strains unless otherwise indicated; further tests with resistant strains of whitefly have shown that many of the compounds of the formula III are highly active against resistant strains.

The whitefly activity test with (BT (SUD-S)) was repeated using a resistant strain of whitefly (Ned ½). The Ned ½ strain is a composite collection which was collected in the Netherlands in 1992 from Gerbera and Bouvardia by ICI Netherlands and exhibits high resistance to pyrethroid insecticides, such as cypermethrin, organophosphate and carbamate insecticides and the insect growth regulator buprofezin.

The results of these tests are set out in Table 7 below. The values given are $LC_{50}$ (ppm solution of test compound).

TABLE 7

| Compound of Example No. | BT (Ned 1/2) ($LC_{50}$) |
|---|---|
| 25 | 0.1 |
| B | 100 |

Compound B=Example 1, Table 1 of DE 3801743 A1 which is 2-hydroxy-3-(4-t-butylcyclohexyl)-naphthalene-1,4-dione The method of Example 22 was repeated using a preferred compound of Formula III, results being shown in Table 8.

TABLE 10

Activity of compounds of Examples 24 to 33 against insect and acarid pests

| Compound of Example No. | PC $LD_{50}$ (µg/insect) | MD $LD_{50}$ (µg/insect) | MP % kill 100 ppm | TU $LC_{50}$ (ppm/insect) | BT $LC_{50}$ (ppm/insect) |
|---|---|---|---|---|---|
| 24 | — | NA | 44 | 48 | 33 |
| 25 | 5 | 1.9 | 22 | 28 | 0.1 |
| 26 | 2.9 | 13 | NA | >100 | 2.9 |
| 27 | 4.7 | 6.0 | NA | c80 | 0.9 |
| 28 | — | 14 | 5 | 40 | 24 |
| 30 | <20 | 15 | NA | 6 | c50 |
| 31 | 5 | 6 | 5 | c50 | 4.7 |
| 32 | <2 | 3.6 | 50 | 2.9 | 3.6 |
| 33 | 2.8 | 5.7 | 30 | 2.3 | 5.1 |

By comparison a prior art compound, Example 1, Table 1 of DE 3801743 A1 which is 2-hydroxy-3-(4-t-butylcyclohexyl)-naphthalene-1,4-dione (Formula II: n=0; m=0; $R^1+R^2$ together and $R^7+R^8$ together both represent =O; $R^3$=—OH; —$CR^4R^5$—=4-t-butylcyclohexyl; but $R^6$=H therefore not covered by formula I or II), was tested against these same pests and gave an MD $LD_{50}$ of 15.5, a PC $LD_{50}$ of 0.53, a TU (GSS) $LC_{50}$ of 44 and a BT(SUD-S) $LC_{50}$ of 18.

Fungitoxicity of coded compounds to isolates of *Aspergillus niger*, *Pyricularia oryzae* (=*Magnaporthe grisea*) and *Rhizoctonia solani* was tested in vitro by the methods described in Example 23 using a preferred compound of formula (III).

The results of these tests are set out in Table 11 below. The values given are % inhibition of growth in colony diameter in agar plates.

TABLE 11

| Compound of Example No. | Fungus | Activity at 100 mg $l^{-1}$ | Activity at 5 mg $l^{-1}$ | Activity at 1 mg $l^{-1}$ |
|---|---|---|---|---|
| 25 | A. niger | 45 | | |
| 25 | P. oryzae | 94 | | |
| 25 | R. solani | 93 | | |
| Prochloraz | A. niger | | | 97.8 |
| Carbendazim | P. oryzae | | 99.8 | 14.7 |
| Carbendazim | R. solani | | 82.4 | 3.3 |

In addition, tests have shown that the compounds of formula (III) exhibit good fungicidal activity against a broad spectrum of fungi which cause diseases in both cereal and broad leaved crops. Particularly, good activity has been observed against fungi of the genera Erysiphe, especially *Erysiphe graminis,* and Botrytis, especially Botrytisfabae and *Botrytis cinerea,* as well as the genera Rhizoctonia, Pyricularia and Aspergillus as illustrated above.

Example 35

Preparation of 2-(2.2-dimethylpropyl)-3-hydroxy-naphthalene-1 4-dione

This compound was prepared by the general methods as described in Examples 1 to 15. Lawsone (0.15 g), 3,3-dimethylbutyric acid (0.15 g), and silver nitrate (0.15 g) were heated in a mixture of acetonitrile (5 ml) and water (5 ml) at 60–65° C. A solution of ammonium peroxysulphate (0.3 g) in water (5 ml) was added dropwise and the mixture heated for 1 hour and then processed as for Example 3 to yield the title compound. The crude product was purified on a silica gel column using 20% diethyl ether in petroleum ether eluant and recrystallised from petroleum ether to yield 38 mg of the title compound.

Example 36

Preparation of 2-(3.3-dimethylbutyl)-3-hydroxy-naphthalene-1.4-dione

Sodium hydroxide solution (1M; 100 ml) was added to a solution of 2-ethanoyloxy-3-(3,3-dimethylbutyl)-naphthalene-1,4-dione (3.5 g)(see Example 44) in THF (100 ml) at room temperature and stirred for 4 hours. The THF was removed under vacuum and the resultant solution was washed with diethyl ether (3x). The aqueous layer was acidified then extracted with diethyl ether (x3), the combined extracts washed with water, dried over magnesium sulphate then evaporated to dryness under vacuum to yield 3 g title compound.

Example 37

Preparation of 2-(4.4-dimethylpentyl)-3-hydroxy-naphthalene-1 4-dione 3,3-dimethyl butan-1-ol (1.3 g) was stirred for 2 hours in dichloromethane (30 ml) with pyridinium chlorochromate (5.5 g) at room temperature, diluted with ether and filtered. Wittig reagent $Ph_3P=CH-CO_2C_2H_5$ (carbethoxymethylenetriphenylphosphorane)(3.6 g) was added to the filtrate and stirred overnight. The mixture was evaporated under vacuum and the residue purified by silica gel chromatography to yield 1.25 g of ethyl 5,5-dimethylhex-2-enoate.

This product was dissolved in a mixture of THF (20 ml) and 2M potassium hydroxide (10 ml), stirred for 2 hours at room temperature, diluted with water, washed with ether (2×30 ml), the aqueous layer acidified then extracted with ether (2×30 ml). The combined extracts were washed with water, dried over magnesium sulphate and the solvent evaporated to give 5,5-dimethylhex-2-enoic acid.

This acid was reacted with benzoyloxynaphthalene-1,4-dione, hydrolysed by the method of Example 28 to give 2-(4,4-dimethylpent-lenyl)-3-hydroxy-naphthalene-1,4-dione. The product so provided was hydrogenated by the method of Example 1(c) to give the title compound (406 mg).

Example 38

Preparation of 2-(5.5-dimethylhexyl)-3-hydroxy-naphthalene-1,4-dione 2-(5,5-dimethylhex-2-enyl)-3-hydroxynaphthalene- 1,4-dione(3 91 mg) prepared in Example 45 was dissolved in ethyl acetate (15 ml) and hydrogenated as in Example 1(c) using hydrogen and 100 mg of Pd/C catalyst to provide 371 mg title compound.

Examples 39 to 41

Preparation of the corresponding 2-(6,6-dimethylheptl), 2-(7,7-dimethyloctyl) and 2-(8,8-dimethylnonyl) compounds was carried out using commercially available starting materials by analogous methods to those of Example 48 with hydrogenation as described in Example 1(c) using $PtO_2$ in methanol instead of Pd/C.

Example 42

Preparation of 2-(3.3-dimethyl-but-1-enyl)-3-hydroxy-naphthalene-1.4- dione

Lawsone (2-hydroxynaphthalene-1,4-dione) (1.4 g) and 3,3-dimethyl-butanal (1.0 g) were dissolved in 20 ml THF at room temperature and 795 µl pyrrolidine added before stirring the reaction for a further 20 minutes. The solvent was removed under vacuum and the residue dissolved in benzene (40 ml) before addition of p-toluenesulphonic acid (2.3 g). The mixture was refluxed for 1 hour, cooled then diluted with ether before the organic phase was washed with sodium bicarbonate solution, followed by one wash with dilute HCl and one wash with water followed by drying under vacuum. The product was purified by chromatograpy using 10% EtOAc/petroleum ether eluant and then crystallised from methanol to yield 260 mg; m.p. 126–128° C.

Example 43

Preparation of 2-(6,6-dimethylhep-4-enyl)-3-hydroxy-naphthalene-1,4-dione

A solution of 2-(7,7-dimethyloct-5-enyl)-3-hydroxynaphthalene-1,4-dione (0.1 g) (see Example 44), 30% hydrogen peroxide (60 µl), aqueous sodium carbonate (36 mg in 1 ml) in degassed dioxane (1 ml) was heated at 70° C. for 40 minutes under nitrogen until the solution became colourless. 20% aqueous copper (II) sulphate (30 µl) was added and when bubbling ceased 25% aqueous sodium hydroxide (0.6 ml) and 20% aqueous copper (II) sulphate (1.5 ml) were added and the mixture stirred at 70° C. for 30 minutes. On cooling 2N hydrochloric acid (5 ml) was added and the product extracted with diethyl ether (3x) and processed as for Example 48.

The crude product was purified by silica gel chromatography using 10% diethyl ether/petrol as eluent to give 50 mg of the title compound.

Example 44

Preparation of 2-(7.7-dimethyloct-5-enyl)-3-hydroxy-naphthalene-1.4-dione

This compound was prepared by use of a procedure analogous to that used in Example 48 below followed by that of Example 36.

Example 45

Preparation of 2-(5,5-dimethylhex-1-enyl)-3-hydroxy-naphthalene-1,4-dione

Ethyl 5,5-dimethylhexanoate (1.87 g) (prepared in Example 34 with esterification), was dissolved in 30 ml of THF and lithium aluminium hydride (2 g) added portionwise. The reaction was stirred for 2 hours at 0° C. before quenching with 2 ml 15% NaOH and 6 ml water before diluting with dichloromethane and filtering through CELITE (RTM) and the solvent evaporated to give 5,5-dimethylhexanol product (1.1 g) as a slightly volatile liquid. This alcohol was dissolved in 30 ml dichloromethane containing pyridinium chlorochromate and stirred at room temperature to convert it to the corresponding aldehyde, 5,5-dimethylhexanal.

The aldehyde (8.46 mmol) was coupled to lawsone following the procedure set out in Example 42 using lawsone (1.18 g),THF (20 ml), pyrrolidine (672 µl), benzene (40 ml) and p-toluenesulphonic acid (1.95 g). 391 mg of the title compound was isolated after purification.

Examples 46–47

The ethanoyloxy derivatives of the 3-(t-butyl) compound (Example 46; of formula (II)) and of the compound of Example 36 (Example 47) were prepared by the method of Example 2.

Example 48

Alternative preparation of 2-ethanoyloxy-3-(3,3-dimethylbutyl)-naphthalene-1.4-dione (Example 47)

1-Chloro-3,3-dimethylbutane (log) was added dropwise to magnesium turnings (2 g) with an initiating amount of iodine crystals in dry diethyl ether (100 ml) and Grignard formation allowed to proceed to completion over 1 hour. The mixture was poured onto dry ice (50 g) very slowly and 0.5 N sodium hydroxide added and the basic aqueous layer provided extracted with diethyl ether (x2). The basic aqueous layer was acidified and extracted with diethyl ether which was dried over magnesium sulphate, filtered then evaporated under vacuum to yield 7.2 g of 4,4-dimethyl pentanoic acid.

4,4-dimethylpentanoate (0.6 g) obtained above, 2-benzyloxynaphthalene-1,4-dione (1 g) and silver nitrate (0.8 g) were heated in a stirred mixture of acetonitrile (25 ml) and water (25 ml) at 60–65° C. A solution of ammonium peroxysulphate (1.5 g) in water (10 ml) was added dropwise and the mixture heated for an hour before being cooled to room temperature and processed as for Example 3 to yield 0.37 g title compound.

Example 49

Preparation of 2-ethanoyoxy-3-(10,10-dimethylundecan-7-enyl)-naphthalene-1,4-dione 8-triphenylphosphonium octanoic acid bromide salt (2.43 g) was prepared by reacting triphenyl phosphine with 8-bromooctanoic acid in xylene solvent under reflux conditions, and removing the solvent. The residue was dissolved in THF (20 ml)/DMSO (2 ml) and butyllithium (2.5M; 4 ml) in hexane (4 ml) was added dropwise at 0° C. After warming to room temperature over 30 minutes 3,3-dimethylbutanal (0.5 g) in THF (5 ml) was added dropwise and the mixture stirred at room temperature for 3 hours. Water and dilute hydrochloric acid were added and the mixture extracted with diethyl ether(x3). Pure product 11,11-dimethyldodecan-8-enoic acid (0.4 g) was provided after silica gel column chromatography.

This acid (0.34 g) was reacted with 2-ethanoyloxynaphthalene-1,4-dione (0.4 g) using the method of Example 47 to give 26 mg title compound.
Further compounds in tables below were synthesized using these general methods.

TABLE 12

Compounds of Formula (IV) wherein $R^1$ with $R^2$, and $R^7$ with $R^8$ are =O and n = 0, + Compound of Formula (II) where m is 0*

| Compound of Example No. | $R^3$ | m | A | $R^4$ | $R^5$ | $R^6$ | mp or nD |
|---|---|---|---|---|---|---|---|
| 35 | OH | 1 | —CH$_2$— | CH$_3$ | CH$_3$ | CH$_3$ | 115–116° C. |
| 36 | OH | 1 | —(CH$_2$)$_2$— | CH$_3$ | CH$_3$ | CH$_3$ | 119–120° C. |
| 37 | OH | 1 | —(CH$_2$)$_3$— | CH$_3$ | CH$_3$ | CH$_3$ | 119° C. |
| 38 | OH | 1 | —(CH$_2$)$_4$— | CH$_3$ | CH$_3$ | CH$_3$ | 82–84° C. |
| 39 | OH | 1 | —(CH$_2$)$_5$— | CH$_3$ | CH$_3$ | CH$_3$ | |
| 40 | OH | 1 | —(CH$_2$)$_6$— | CH$_3$ | CH$_3$ | CH$_3$ | 62–63° C. |
| 41 | OH | 1 | —(CH$_2$)$_7$— | CH$_3$ | CH$_3$ | CH$_3$ | |
| 42 | OH | 1 | —CH=CH— | CH$_3$ | CH$_3$ | CH$_3$ | 126–128° C. |
| 43 | OH | 1 | —(CH$_2$)$_3$CH=CH— | CH$_3$ | CH$_3$ | CH$_3$ | 79–80° C. |
| 44 | OH | 1 | —(CH$_2$)$_4$CH=CH— | CH$_3$ | CH$_3$ | CH$_3$ | 69–70° C. |
| 45 | OH | 1 | —CH=CH—(CH$_2$)$_2$— | CH$_3$ | CH$_3$ | CH$_3$ | |
| 46* | OCOCH$_3$ | 0 | — | CH$_3$ | CH$_3$ | CH$_3$ | 57–58° C. |
| 47 | OCOCH$_3$ | 1 | —(CH$_2$)$_2$— | CH$_3$ | CH$_3$ | CH$_3$ | 75–76° C. |
| 49 | OCOCH$_3$ | 1 | —(CH$_2$)$_6$—CH=CH—CH$_2$— | CH$_3$ | CH$_3$ | CH$_3$ | 1.5286 |
| 50 | OH | 1 | —(CH$_2$)$_2$— | CH$_3$ | CH$_3$ | CH=CH2 | |

TABLE 13

Pesticidal activity of compounds of Formula (IV)

| Compound of Example No. | PC LD$_{50}$ (μg/insect) | MD LD$_{50}$ (μg/insect) | MP % kill 100 ppm | TU LC$_{50}$ (ppm/insect) | BT LC$_{50}$ (ppm/insect) |
|---|---|---|---|---|---|
| 35 | 4.6 | 1.2 | — | — | c12 |
| 36 | 1.3 | NA | c24 | 36 | c7 |
| 37 | NA | NA | c70 | 2.9 | 16 |
| 38 | c8 | 5.3 | c100 | 3.5 | c60 |
| 39 | — | c5 | c100 | 9.6 | 21 |
| 40 | — | c5 | c100 | 5 | 13 |
| 42 | 3.6 | NA | — | c100 | 17 |
| 43 | — | — | c100 | 11.5 | c60 |
| 44 | — | c10 | c100 | 4.3 | c100 |
| 46 | c15 | 2.3 | c60 | c500 | NA |
| 47 | c1 | 2.2 | c100 | c20 | 2.1 |
| 49 | c10 | c18 | c15 | 2.3 | NA |
| 50 | — | — | — | 6.5 | 16 |

TABLE 14

Comparative Examples R$^1$R$^2$ and R$^7$R$^8$ = =O; R$^3$ = OH

| Naphthalene 3 position | PC LD$_{50}$ (μg/insect) | MD LD$_{50}$ (μg/insect) | MP % kill 100 ppm | TU LC$_{50}$ (ppm/insect) | BT LC$_{50}$ (ppm/insect) |
|---|---|---|---|---|---|
| —H | NA | NA | — | NA | NA |
| —CH$_3$ | NA | NA | — | NA | NA |
| —CH$_2$CH$_3$ | NA | NA | — | NA | NA |
| —(CH$_2$)$_2$CH$_3$ | c10 | NA | — | c1000 | 80 |
| —(CH$_2$)$_3$CH$_3$ | c5 | c10 | — | 65 | 13 |
| —(CH$_2$)$_4$CH$_3$ | c7 | NA | — | 16 | 17 |
| —(CH$_2$)$_5$CH$_3$ | c7 | c20 | 0 | 170 | 9.4 |
| —(CH$_2$)$_7$CH$_3$ | 0.78 | 1.9 | — | c1000 | 19 |
| —(CH$_2$)$_9$CH$_3$ | 1.9 | NA | — | 5.5 | >100 |
| —(CH$_2$)$_{10}$CH$_3$ | c0.4 | NA | — | 1.4 | >100 |
| —(CH$_2$)$_{11}$CH$_3$ | NA | NA | 0 | <60 | >100 |
| —(CH$_2$)$_{13}$CH$_3$ | NA | NA | — | 1.3 | NA |

Examples 51–53

Synthesis of naphthalene-1,4-diones substituted at positions 5–8 on the naphthalene ring Example 51

Preparation of 2-(t-butyl)-3-hydroxy-6-methyl-naphthalene-1,4-dione and 2-(t-butyl)-3-hydroxy-7-methyl-naphthalene-1,4-dione (a) Preparation of 6-methyl-naphthalene-1,4-dione A solution of 1,4-benzoquinone (13.9 g, 128 mmol) and isoprene (13.1 ml, 131 mmol) was stirred in glacial acetic acid (44 ml) for 68 hours at room temperature. The mixture was diluted with water (44 ml) and refluxed for 1½ hours. The mixture was cooled to room temperature and acetic acid (84 ml) and chromic acid [chromium trioxide (29.4 g) in water (30 ml)] was added sequentially, before refluxing for a further 1½ hours. After cooling, the mixture was diluted with water (200 ml) and extracted with ether (3×50 ml). The combined ether fractions were washed with dilute sodium hydroxide solution (2M; 2×50 ml), water (2×50 ml), saturated sodium chloride solution (50 ml) and dried over magnesium sulphate. Filtration and evaporation of solvent under reduced pressure, and repeated recrystallisation from petroleum ether yielded the title compound (7 g).

(b) 2-Amino-6 and 7-methyl-1,4-naphthalene-1,4-diones

To a stirred solution of 6-methyl naphthalene-1,4-dione (2.1 g, 12 mmol) in glacial acetic acid (60 ml) at room temperature was added a solution of sodium azide (1.58 g) in water (5 ml). The mixture was stirred for 2 days before diluting with water (200 ml) and, after stirring for a further 15 minutes, was filtered. The filtrate was neutralised with sodium bicarbonate and extracted with chloroform (3×25 ml). The combined chloroform extracts were washed with saturated sodium bicarbonate solution, brine and dried (CaSO$_4$). Filtration and evaporation of solvent under reduced pressure and silica gel chromatography yielded the title compound (100 mg) as a 3:2 mixture of isomers.

(c) 2-Hydroxy-6- and -7-methyl-naphthalene-1,4-diones

The aminomethyl naphthalene-1,4-dione mixture from (b)(200 mg) was refluxed in water (20 ml) and concentrated sulphuric acid (10 ml) for 20 minutes. The cooled mixture was poured into ice/water (50 g) and extracted with ether (3×25 ml). The combined ether extracts were washed with water, saturated NaHCO$_3$, water, saturated NaCl solution and dried (MgSO$_4$). Filtration and evaporation of solvent and purification by silica gel column chromatography yielded the title compound (68 mg).

(d) Preparation of 2-(t-butyl)-3-hydroxy-6 and 7-methyl-3-hydroxy-naphthalene-1,4-diones Standard peroxysulphate/silver nitrate radical addition on the aminomethyl compound (64 mg, 0.34 mmol), trimethylacetic acid (52 mg, 0.51 mmol), yielded the title compound as a 3:2 mixture of isomers (12 mg).

Example 52

Preparation of 2-(t-butyl)-6 and 7-dimethyl-3-hydroxy-naphthalene-1,4-diones

Steps (a) to (d) above were repeated, replacing isoprene with 2,3-dimethyl-1,3-butadiene.

Example 53

Preparation of 2-(t-butyl)-3-hydroxy-5 and 8-methyl-1,4-naphthalene-1,4-diones

Steps (a) to (d) above were repeated, replacing isoprene with piperylene.

(a) Preparation of 6-methyl-1,4-naphthalene-1,4-dione

A solution of 1,4-benzoquinone (13.9 g, 128 mmol) and isoprene (13.1 ml, 131 mmol) was stirred in glacial acetic acid (44 ml) for 68 hours at room temperature. The mixture was diluted with water (44 ml) and refluxed for 1½ hours. The mixture was cooled to room temperature and acetic acid (84 ml) and chromic acid [chromium trioxide (29.4 g) in water (30 ml)] was added sequentially, before refluxing for a further 1½ hours. After cooling, the mixture was diluted with water (200 ml) and extracted with ether (3×50 ml). The combined ether fractions were washed with dilute sodium hydroxide solution (2M; 2×50 ml), water (2×50 ml), saturated sodium chloride solution (50 ml) and dried over magnesium sulphate. Filtration and evaporation of solvent under reduced pressure, and repeated recrystallisation from petroleum ether yielded the title compound (7 g).

Toxicity data

In addition to the specific insecticidal and acaricidal tests described above, compounds of the present invention were submitted for further tests relating to toxicity to mammals and so-called friendly species such as *Chrysloperla carnea*, *Aleochora bilineata* and *Coccinella septempunctata*.

The whole body $LD_{50}$ in rats for the compound of Example 25, 2-hydroxy-3-(1'-methylcyclohexyl)-naphthalene-1,4-dione, was found to be 2786 mg/Kg body weight, indicating it to be significantly safer in mammalian toxicity than many standard insecticides currently commercially available.

$LD_{50}$ values of greater than 1000 ppm/individual were found for several compounds tested on *Chrysloperla carnea*, *Aleochora bilineata* and *Coccinella septempunctata*.

We claim:

1. 1. A compound of formula (I)

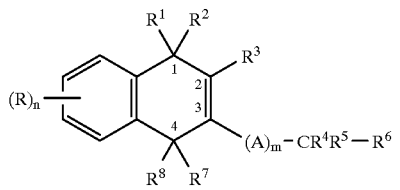

or a salt thereof, in which
n represents an integer from 0 to 4; m represents an integer 0 or 1;
   each R independently represents a halogen atom or a nitro, cyano, hydroxyl, alkyl, alkenyl, haloalkyl, haloalkenyl, alkoxy, haloalkoxy, haloalkenoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group;
   $R^1$ and $R^2$ each independently represent an optionally substituted alkoxy group or together represent a group $=O$, $=S$ or $=N-OR^9$, where R9 represents a hydrogen atom or an optionally substituted alkyl group;
   $R^3$ represents a group $OR^{10}$ where $R^{10}$ represents a hydrogen atom, an optionally substituted aryl or aralkyl group, or a group $-CO-R^{11}$, $-CO-O-R^{11}$, $-SOR^{11}$, $-SO_2-R^{11}$, $-P(X)(OR^{12})(OR^{13})$, $-P(X)(R^{12})(OR^{13})$, $-P(OR^{12})(OR^{13})$ or $-P(R^{12})(OR^{13})$ where $R^{11}$ represents a hydrogen atom, an optionally substituted alkyl, alkenyl, aryl or aralkyl group or a group-$NR^{12}R^{13}$; $R^{12}$ and $R^{13}$ independently representing a hydrogen atom or an optionally substituted alkyl group and X represents an oxygen or sulfur atom;
   $R^6$ represents an optionally substituted alkyl, alkenyl, alkynyl, cycloalkyl, cycloalkenyl, aryl, alkoxy, alkenyloxy, alkynyloxy, cycloalkyloxy, cycloalkenyloxy or aryloxy group;
   $R^7$ and $R^8$ independently represent an optionally substituted alkoxy group or together represent a group $=O$, $=S$ or $=N-OR^9$, where $R^9$ is as previously defined;

$R_4$ and $R_5$ each independently represent a halogen atom or an optionally substituted alkyl or alkenyl group, or together with the interjacent carbon atom represent an optionally substituted cycloalkyl or cycloalkenyl ring; and
   A represents a straight or branched chain alkyl or alkenyl group, which may be optionally substituted, an acyclic carbon chain of which links the 3 position of the naphthalene ring shown and the moiety $-CR^4R^5R^6$; with the provisos that when $R^1$ with $R^2$, and $R^7$ with $R^8$ are groups $=O$ and n=0, (i) when $R^4$ and R5 are methyl, m is 0 and $R^6$ is ethenyl, then $R^3$ is not hydroxyl or ethanoyloxy, (ii) when $R^4$ and $R^5$ are methyl, m is 0 or m is 1 where A is $-CH_2-$ or $(CH_2)_2-$ and $R^3$ is hydroxyl, then $R^6$ is not methyl, (iii) when $R^4$ and $R^5$ are methyl, m is 1 where A is $-(CH_2)_2-$ and $R^3$ is hydroxyl, then $R^6$ is not chloro, (iv) when $R^4$ and $R^5$ together with the interjacent carbon atom form a cyclohexyl ring, m is 1 where A is $-CH_2$ and $R^3$ is hydroxyl, then $R^6$ is not methyl, (v) when $R^4$ and $R^5$ are methyl, m is 1 where A is $-CH_2-$ and $R^3$ is hydroxyl, then $R^6$ is not hydroxymethyl, and (vi) when m is 0, then $R^6$ represents a group of $C_{1-6}$ carbons in length, or the 2,6-dimethyl-2,6-octadienoate ester thereof.

2. A compound as claimed in claim 1 wherein $R^1$ and $R^2$, and/or $R^7$ and $R^8$ each independently represent a $C_{1-4}$ alkoxy group or $R^1$ with $R^2$ and/or $R^7$ with $R^8$ together represent a group $=O$.

3. A compound as claimed in claim 1 wherein $R^6$ represents a $C_{1-16}$ alkyl, $C_{2-16}$ alkenyl, $C_{1-16}$ haloalkyl, $C_{2-16}$ haloalkenyl, $C_{1-16}$ alkanoylalkyl, $C_{1-16}$ alkoxyalkyl, $C_{1-16}$ alkoxy, $C_{1-16}$ haloalkoxy or $C_{1-16}$ alkoxyalkoxy group.

4. A compound as claimed in claim 3 wherein $R^6$ represents a group of $C_{1-6}$ carbons in length.

5. A compound as claimed in claim 1 which it is a naphthalene-1,4-dione.

6. A compound as claimed in claim 1 wherein $R^4$ and $R^5$ independently represent a $C_{1-4}$ alkyl, $C_{1-4}$ haloalkyl, $C_{2-4}$ alkenyl, $C_{2-4}$ haloalkenyl or together with the interjacent carbon atom, represent a cycloalkyl or cycloalkenyl group which is optionally substituted with halogen, alkyl, haloalkyl, alkenyl or haloalkenyl.

7. A compound as claimed in claim 1 of formula (II)

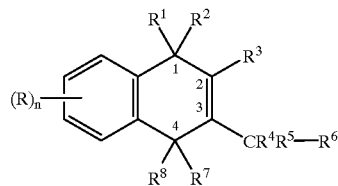

or a salt thereof
in which R, $R^1$, $R^2$, $R^3$, $R^6$, $R^7$ and $R^8$ and n are as defined for formula I and $R^4$ and $R^5$ represent a halogen or an optionally substituted alkyl or alkenyl group.

8. A compound as claimed in claim 7 wherein n is 0; $R^1$ with $R^2$, and $R^7$ with $R^8$ are both $=O$; $R^4$ and $R^5$ each independently represent a $C_{1-4}$ alkyl or $C_{1-4}$ haloalkyl group and $R^6$ represents a $C_{1-7}$ alkyl, $C_{1-7}$ haloalkyl, $C_{17}$ alkoxyalkyl, $C_{1-7}$ alkoxy, $C_{1-7}$ alkoxyalkoxy, $C_{2-7}$ alkenyl, $C_{2-C7}$ haloalkenyl or $C_2$-$C_7$ alkoxyalkenyl group.

9. A compound as claimed in claim 8 wherein $R^6$ represents a $C_{1-6}$ alkyl, $C_{1-6}$ haloalkyl, $C_2$ alkenyl or $C_2$ haloalkenyl group.

10. A compound as claimed in claim 1 of formula (III)

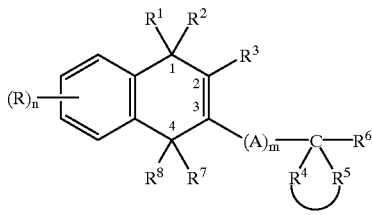

(III)

wherein
n, m, A, R, $R^1$, $R^2$, $R^3$, $R^6$, $R^7$ and $R^8$ are as defined for general formula (I); and $R^4$ and $R^5$ together with the interjacent carbon atom represent an optionally substituted cycloalkyl or cycloalkenyl group.

11. A compound as claimed in claim 10 wherein $R^1$ with $R^2$, and $R^7$ with $R^8$ are both =O; n is 0; $R^4$ and $R^5$ together with the interjacent carbon atom represent a fully saturated cycloalkyl ring which is optionally substituted; and $R^6$ represents a $C_{1-16}$ alkyl or $C_{2-16}$ alkenyl group optionally substituted by halogen.

12. A compound as claimed in claim 11 wherein $R^4$ and $R^5$ together with the interjacent carbon atom represent a $C_{4-8}$ saturated cycloalkyl ring optionally substituted with halogen, alkyl, haloalkyl, alkenyl or haloalkenyl.

13. A compound as claimed in claim 12 wherein $R^4$ and $R^5$ together with the interjacent carbon atom represent a $C_{5-8}$ cycloalkyl ring optionally substituted with halogen, alkyl, haloalkyl, alkenyl, or haloalkenyl, and $R^6$ is a $C_{1-6}$ alkyl, $C_{2-6}$ alkenyl, $C_{1-6}$ haloalkyl or $C_{2-6}$ haloalkenyl group or a halogen and $R^3$ is hydroxy or acetoxy.

14. A compound as claimed in claim 13 wherein $R^4$ and $R^5$ together with the interjacent carbon atom represent an optionally substituted cyclohexyl ring.

15. A compound as claimed in claim 12 wherein $R^4$ and $R^5$ together with the interjacent carbon atom represent an optionally substituted cyclohexyl ring and $R^6$ represents an optionally halogenated $C_{1-2}$ alkyl or $C_2$ alkenyl group.

16. A compound as claimed in claim 15 wherein m is 0.

17. A compound as claimed in claim 15 wherein m is 1 and A is —$CH_2$—.

18. A compound as claimed in claim 1 of formula (IV)

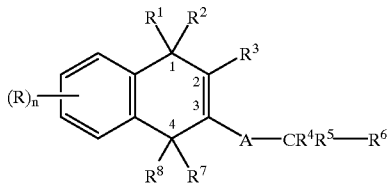

(IV)

wherein
n, A, R, $R^1$, $R^2$, $R^3$, $R^6$, $R^7$ and $R^8$ are as defined for formula (I); and $R^4$ and $R^5$ each independently represent a halogen or optionally substituted alkyl or alkenyl group.

19. A compound as claimed in claim 18 wherein $R^1$ with $R^2$, and $R^7$ with $R^8$ are both =O; and A is a $C_{3-8}$ alkyl or alkenyl chain, which may be substituted by halogen or a branch chain which may be halogenated.

20. A compound as claimed in 18 wherein $R^4$, $R^5$ and $R^6$ are independently selected from $C_{1-6}$ alkyl, $C_{1-6}$ haloalkyl, $C_{2-6}$ alkenyl or $C_{2-6}$ haloalkenyl.

21. A compound as claimed in claim 18 wherein A is a group —$(CH_2)_a$— wherein a is an integer from 1 to 7, or —$(CH_2)_a$—CH=CH—$(CH_2)_b$— where a and b are integers which add up to 0 to 6, or an analogue of these wherein one or more of the carbon atoms in the these groups are substituted by alkyl, haloalkyl, alkenyl, aloalkenyl or halogen.

22. A compound as claimed in claim 21 wherein a and b add up to 0 to 3.

23. A method of combatting pests at a locus which comprises treating the locus with a compound of the formula (I)

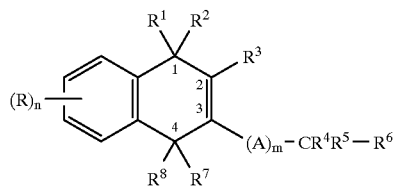

(I)

or a salt thereof, in which
n represents an integer from 0 to 4; m represents an integer 0 or 1;
each R independently represents a halogen atom or a nitro, cyano, hydroxyl, alkyl, alkenyl, haloalkyl, haloalkenyl, alkoxy, haloalkoxy, haloalkenoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group; wherein $R^1$ and $R^2$ each independently represent an optionally substituted alkoxy group or together represent a group =O, =S or =N—$OR^9$ represents a hydrogen atom or an optionally substituted alkyl group;
$R^3$ represents a group $OR^{10}$ where $R^{10}$ represents a hydrogen atom, an optionally substituted aryl and aralkyl group, or a group —CO—$R^{11}$, —CO—O—$R^{11}$, —$SOR^{11}$, —$SO_2$—$R^{11}$, —P(X)($OR^{12}$)($OR^{13}$), —P(X)($R^{12}$)($OR^{13}$), —P($OR^{12}$)($OR^{13}$) or —P($R^{12}$)($OR^{13}$) where $R^{11}$ represents a hydrogen atom, an optionally substituted alkyl, alkenyl, aryl or aralkyl group or a group—$NR^{12}R^{13}$; $R^{12}$ and $R^{13}$ independently representing a hydrogen atom or an optionally substituted alkyl group and X represents an oxygen or sulfur atom;
$R^6$ represents an optionally substituted alkyl, alkenyl, alkynyl, cycloalkyl, cycloalkenyl, aryl, alkoxy, alkenyloxy, alkynyloxy, cycloalkyloxy, cycloalkenyloxy or aryloxy group; $R^7$ and $R^8$ independently represent an optionally substituted alkoxy group or together represent a group =O, =S or =N—$OR^9$, where $R^9$ is a previously defined; and wherein $R_4$ and $R_5$ each independently represent a halogen atom or an optionally substituted alkyl or alkenyl group or together with the interjacent carbon atom represent an optionally substituted cycloalkyl or cycloalkenyl ring; and
A represents a straight or branched chain alkyl or alkenyl group, which may be optionally substituted, an acyclic carbon chain of which links the 3 position of the naphthalene ring shown and the moiety —$CR^4R^5R^6$: with the proviso that when $R^1$ with $R^2$, and $R^7$ with $R^8$ are groups =O and n=0, when $R^4$ and $R^5$ are methyl; m is 1 A is —$CH_2$— and $R^3$ is hydroxyl, then $R^6$ is not hydroxymethyl or the 2,6-dimethyl-2,6-octadienoate ester thereof.

24. A method as claimed in claim 23 wherein the pests are insects, acarids and/or fungi.

25. A method as claimed in claim 23 wherein the compound is of formula (II), (III) or (IV).

26. A method as claimed in claim 25 wherein the locus comprises the pests or environments subject to or subjected to attack by the pests.

27. A process for the preparation of a compound of formula (I) wherein m is 0 comprising reacting a compound of the general formula (V)

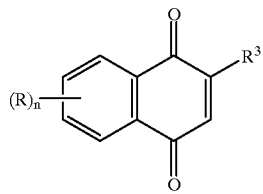

(V)

in which n, R and $R^3$ are as defined in formual (I), with a compound of the general formula (VI)

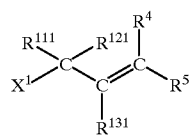

(VI)

in which X represents a leaving group, $R^{111}$, $R^{121}$ and $R^{131}$ each independently represent a hydrogen atom or an optionally substituted alkyl group and $R^4$ and $R^5$ are as defined in formula (I) to produce a compound of the formula (VII)

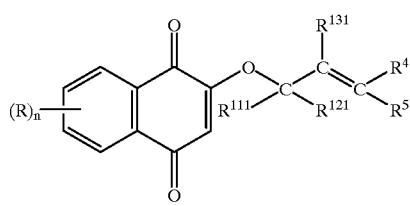

(VII)

in which n, R, $R^{111}R^{121}$, $R^{131}$, $R^4$ and $R^5$ are as defined above;
and the compound of formula (VII) is then heated in a suitable solvent to effect a Claisen-type rearrangement resulting in a compound of the formula (VIII)

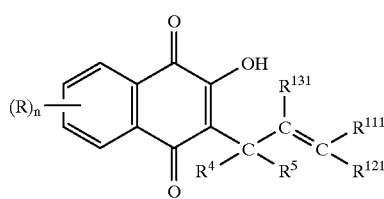

(VIII)

28. A process as claimed in claim 27 wherein X represents a hydroxyl group and the reaction is out under Mitsunobu conditions.

29. A process as claimed in claim 27 wherein X represents a halogen atom and the reaction is be carried out under alkylating conditions.

30. A process for the preparation of a compound of formula (I) which compromises reacting an aldehyde A—$CR^4R^5R^6$, where A, $R^4$, $R^5$ and $R^6$ are as defined for formula I and A has an aldehyde group at the free end of the acyclic carbon chain instead of the 3-position of the napthalene ring, directly with the compound of formula (V) in a polar organic solvent under alkaline conditions, and then heating the product under acidic conditions in a non-polar solvent to effect elimination of water.

31. A process for the preparation of a compound of formula (I) comprising reacting a compound of the general formula (V)

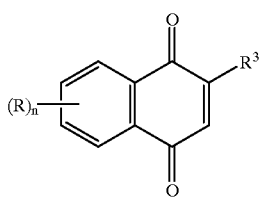

(V)

in which n, R and $R^3$ are as defined above, with a carboxylic acid $CR^4R^5R^6$—(A)$_m$—COOH where A, m, $R^4$, $R^5$ and $R^6$ are as defined for formula I, in the presence of a free radical initiator.

32. A process for the preparation of a compound of formula (I) comprising reacting a compound of the general formula (V)

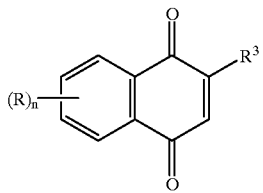

(V)

with a compound of general formula X—(A)$_m$—$CR^4R^5R^6$, wherein A, m, $R^4$, $R^5$ $R^6$ are as defined for formula I and X is a leaving group that leaves to provide the radical $^+$—(A)$_m$—$CR^4R^5R^6$, in the presence of an acid.

33. A process as claimed in claim 32 wherein X is a halogen or a tosyl group.

34. A process as claimed in claim 32 wherein the acid is a Lewis acid.

35. A process as claimed in claim 34 wherein the Lewis acid is aluminium chloride.

36. A composition comprising a compound of formula (I) as defined above, in association with at least one carrier.

37. A composition as claimed in claim 36 which contains from 0.001 to 95% by weight of the active ingredient of formula I.

38. A composition as claimed in claim 36 which contains from 0.001 to 25% by weight of the active ingredient.

39. A compound of formula (VII)

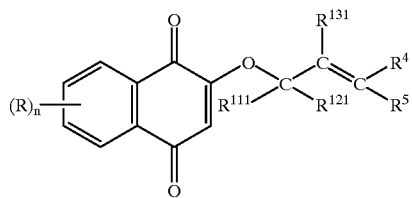

(VII)

wherein n, R, $R^4$ and $R^5$ are as defined in claim, $R^{111}$, $R^{121}$ and $R^{131}$ each independently represents a hydrogen atom or an optionally substituted alkyl group.

40. A process according to claim 27, wherein said leaving group for X is a hydroxyl group or a halogen atom.

41. A process according to claim 40, wherein said halogen atom is a chlorine or bromine atom.

* * * * *